United States Patent
Koga et al.

(10) Patent No.: US 10,087,155 B2
(45) Date of Patent: Oct. 2, 2018

(54) ONIUM SALT, LIQUID COMPOSITION CONTAINING SAID ONIUM SALT AND CELLULOSE, AND CELLULOSE RECOVERY METHOD

(71) Applicant: Koei Chemical Company, Limited, Chiba (JP)

(72) Inventors: Yuko Koga, Sodegaura (JP); Syuko Sakugawa, Sodegaura (JP)

(73) Assignee: KOEI CHEMICAL COMPANY, LIMITED, Osaka-shi, Osaka (JP)

( * ) Notice: Subject to any disclaimer, the term of this patent is extended or adjusted under 35 U.S.C. 154(b) by 0 days.

(21) Appl. No.: 14/649,005

(22) PCT Filed: Dec. 3, 2013

(86) PCT No.: PCT/JP2013/007105
§ 371 (c)(1),
(2) Date: Jun. 2, 2015

(87) PCT Pub. No.: WO2014/087646
PCT Pub. Date: Jun. 12, 2014

(65) Prior Publication Data
US 2016/0009669 A1 Jan. 14, 2016

(30) Foreign Application Priority Data
Dec. 3, 2012 (JP) .................. 2012-263910

(51) Int. Cl.
| C07D 295/04 | (2006.01) |
| C07C 219/06 | (2006.01) |
| C07C 59/125 | (2006.01) |
| C07D 233/58 | (2006.01) |
| C08B 16/00 | (2006.01) |
| C08B 1/00 | (2006.01) |
| C07C 211/63 | (2006.01) |
| C07C 217/08 | (2006.01) |

(52) U.S. Cl.
CPC .......... *C07D 295/04* (2013.01); *C07C 59/125* (2013.01); *C07C 211/63* (2013.01); *C07C 217/08* (2013.01); *C07C 219/06* (2013.01); *C07D 233/58* (2013.01); *C08B 1/003* (2013.01); *C08B 16/00* (2013.01)

(58) Field of Classification Search
CPC .. C07D 295/04; C07D 233/58; C07C 59/125; C07C 219/06; C08B 16/00

USPC .......... 562/587; 536/57; 252/364; 548/335.1
See application file for complete search history.

(56) References Cited

U.S. PATENT DOCUMENTS

2010/0137175 A1* 6/2010 Kunz .................... C07C 51/412
508/463

FOREIGN PATENT DOCUMENTS

| CN | 1596282 A | | 3/2005 |
| CN | 101675023 A | | 3/2010 |
| JP | 2000-154163 A | | 6/2000 |
| JP | 2004-002382 A | | 1/2004 |
| JP | 2005-506401 A | | 3/2005 |
| JP | 2005-247850 A | | 9/2005 |
| JP | WO2008102747 | * | 8/2008 |
| JP | 2010-111707 A | | 5/2010 |
| JP | 2010-526115 A | | 7/2010 |
| JP | 2013-194147 A | | 9/2013 |
| WO | 0329329 A2 | | 4/2003 |
| WO | 2008135482 A2 | | 11/2008 |

OTHER PUBLICATIONS

Pernak et al. Synthesis and properties of ammonium ionic liquids with cyclohexyl substituent and dissolution of cellulose. RSC Advances, 2012, 2, 8429-8438. (published on Jul. 24, 2012).*
Vitz, et al., "Extended dissolution studies of cellulose in imidazolium based ionic liquids," Green Chemistry, vol. 11, pp. 417-424 (2009).
International Search Report dated Mar. 4, 2014 in International Application No. PCT/JP2013/007105.
Office Action dated Apr. 14, 2016 in CN Application No. 201380063127.1.

* cited by examiner

*Primary Examiner* — Yih-Horng Shiao
(74) *Attorney, Agent, or Firm* — Panitch Schwarze Belisario & Nadel LLP

(57) ABSTRACT

The invention relates to an onium salt, a liquid composition containing the onium salt and cellulose, and a method for recovering cellulose. The invention makes it possible to provide an onium salt having an extremely high ability to dissolve cellulose at temperatures of 100° C. or lower. It also makes it possible to provide a liquid composition containing this onium salt and cellulose, as a composition suitable for the recovery of cellulose, and a method for recovering cellulose efficiently by using such a liquid composition containing the onium salt and cellulose.

21 Claims, No Drawings

ONIUM SALT, LIQUID COMPOSITION CONTAINING SAID ONIUM SALT AND CELLULOSE, AND CELLULOSE RECOVERY METHOD

CROSS-REFERENCE TO RELATED APPLICATION

This application is a Section 371 of International Application No. PCT/JP2013/007105, filed Dec. 3, 2013, which was published in the Japanese language on Jun. 12, 2014, under International Publication No. WO 2014/087646 A1, and the disclosure of which is incorporated herein by reference.

TECHNICAL FIELD

The present invention relates to an onium salt, a liquid composition containing the onium salt and cellulose, and a method for recovering cellulose.

BACKGROUND ART

Recently, onium salts have been suggested as a solvent for dissolving cellulose (see, Patent Literature 1 and Non-Patent Literature 1, for example). In Patent Literature 1 describes a method of recycling cellulose by dissolving cellulose in an imidazolium-based onium salt such as 1-butyl-3-methylimidazolium chloride and mixing the obtained cellulose-containing onium salt with water. Non-Patent Literature 1 describes a method in which cellulose is dissolved in an imidazolium-based onium salt such as 1-ethyl-3-methylimidazolium acetate and 1-ethyl-3-methylimidazolium chloride, and a mixture of the obtained cellulose-containing ionic liquid added with dimethyl sulfoxide is mixed with methanol to precipitate the cellulose.

Accordingly, in view of Patent Literature 1 and Non-Patent Literature 1, inventors of the present invention tried dissolving cellulose by using an onium salt such as 1-ethyl-3-methylimidazolium chloride. However, when the onium salt described in Patent Literature 1 and Non-Patent Literature 1 is used, the solubility of cellulose was not fully satisfactory at 100° C. (see, Comparative Evaluation Examples that are described below).

CITATION LIST

Patent Literature

Patent Literature 1: JP 2005-506401 W

Non-Patent Literature

Non-Patent Literature 1: Green Chemistry, 2009, Vol. 11, p. 417-424

SUMMARY OF INVENTION

Technical Problem

An object of the present invention, which is achieved to solve the aforementioned technical problems of the related art, is to provide an onium salt having an extremely high ability to dissolve cellulose at temperatures of 100° C. or lower, compared to conventionally known onium salts. Another object is to provide a liquid composition containing this onium salt and cellulose, as a composition suitable for the recovery of cellulose, and a method for recovering cellulose efficiently by using such a liquid composition containing the onium salt and cellulose.

Solution to Problem

The inventors of the present invention conducted intensive studies on a material that can be used as a solvent for sufficiently dissolving cellulose at temperatures of 100° C. or lower, and completed the present invention accordingly.

Specifically, the present invention provides the following [1] to [13].

[1] An onium salt represented by Formula (1):

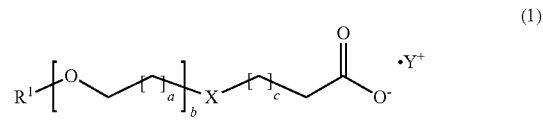

in the formula, a represents an integer of 1 to 3, b represents an integer of 0 to 6, c represents an integer of 0 to 3, $R^1$ represents a hydrocarbon group having 1 to 6 carbon atoms, X represents an oxygen atom or a sulfur atom, and $Y^+$ represents an onium cation.

[2] The onium salt described in [1], in which b is 0 or 1.

[3] The onium salt described in [1], in which a is 1, b is 0 or 1, c is 0 or 1, and $R^1$ is a hydrocarbon group having 1 or 2 carbon atoms.

[4] The onium salt described in any one of [1] to [3], in which $Y^+$ is an onium cation represented by any one of the following Formulae (2) to (4):

Formula (2):

in the formula, $Z^+$ represents a nitrogen ion or a phosphorus ion, and $R^2$ to $R^5$ represent a hydrocarbon group having 1 to 20 carbon atoms which may contain a hetero atom, Formula (3):

in the formula, $R^6$ represents a hydrocarbon group having 4 to 20 carbon atoms which may contain a hetero atom and $R^7$ and $R^8$ represent a hydrocarbon group having 1 to 20 carbon atoms which may contain a hetero atom, with the proviso that $R^8$ does not exist when the nitrogen ion has a double bond, Formula (4):

(4)

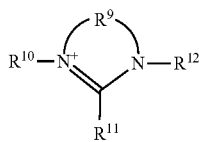

in the formula, $R^9$ represents a hydrocarbon group having 2 to 20 carbon atoms which may contain a hetero atom and $R^{10}$, $R^{11}$, and $R^{12}$ represent a hydrogen atom or a hydrocarbon group having 1 to 20 carbon atoms which may contain a hetero atom.

[5] The onium salt described in [4], in which at least one of $R^2$ to $R^5$ is an alkoxyalkyl group, at least one of $R^7$ and $R^8$ is an alkoxyalkyl group, and at least one of $R^{10}$ to $R^{12}$ is an alkoxyalkyl group.

[6] The onium salt described in [1], in which $Y^+$ is N,N-diethyl-N-methyl-N-(2-methoxyethyl)ammonium or N-ethyl-N-[2-(2-methoxyethoxy)ethyl]-N,N-dimethylammonium.

[7] A mixed onium salt obtained by mixing two or more types of the onium salt described in [1].

[8] A liquid composition comprising cellulose and the onium salt described in [1] or the mixed onium salt described in [7], in which the cellulose is dissolved in the onium salt or the mixed onium salt.

[9] A liquid composition comprising cellulose and a medium containing the onium salt described in [1] or the mixed onium salt described in [7] and an organic solvent, in which the cellulose is dissolved in the medium.

[10] The liquid composition described in [9], in which the organic solvent is at least one organic solvent selected from a group consisting of N,N-dimethylacetamide, dimethyl sulfoxide, and N,N-dimethylformamide.

[11] A method for recovering cellulose comprising dissolving cellulose in a medium containing the onium salt described in [1] or the mixed onium salt described in [7] and the cellulose, and further mixing it with a poor solvent to precipitate the cellulose.

[12] A method for recovering cellulose comprising dissolving cellulose in a medium containing the onium salt described in [1] or the mixed onium salt described in [7] and an organic solvent, and further mixing it with a poor solvent to precipitate the cellulose.

[13] The method for recovering cellulose described in [12], in which the organic solvent is at least one organic solvent selected from a group consisting of N,N-dimethylacetamide, dimethyl sulfoxide, and N,N-dimethylformamide.

Advantageous Effects of Invention

According to the present invention, it is possible to provide an onium salt having an extremely high ability to dissolve cellulose at temperatures of 100° C. or lower. It is also possible to provide a liquid composition containing this onium salt and cellulose, as a composition suitable for the recovery of cellulose, and a method for recovering cellulose efficiently by using such a liquid composition containing the onium salt and cellulose.

DESCRIPTION OF EMBODIMENTS

Hereinbelow, the present invention is explained specifically. The present invention pertains to the onium salt represented by Formula (1) shown above (hereinbelow, it may be referred to as the onium salt (1)). In Formula (1), a represents an integer of 1 to 3, b represents an integer of 0 to 6, c represents an integer of 0 to 3, and it is preferable that b is 0 or 1, and it is more preferable that a is 1, b is 0 or 1, and c is 0 or 1. $R^1$ represents a hydrocarbon group having 1 to 6 carbon atoms, X represents an oxygen atom or a sulfur atom, and $Y^+$ represents an onium cation.

Specific examples of an anion in the onium salt (1) include methoxyacetic acid ion, ethoxyacetic acid ion, propoxyacetic acid ion, (2-methoxyethoxy)acetic acid ion, (2-ethoxyethoxy)acetic acid ion, (2-propoxyethoxy)acetic acid ion, 3-(2-methoxyethoxy)propanoic acid ion, 3-(2-ethoxyethoxy)propanoic acid ion, 3-(2-propoxyethoxy)propanoic acid ion, 3-(3-methoxypropoxy)propanoic acid ion, 3-(3-ethoxypropoxy)propanoic acid ion, 3-(3-propoxypropoxy)propanoic acid ion, 3-[2-(2-methoxyethoxy)ethoxy]propanoic acid ion, 3-[2-(2-ethoxyethoxy)ethoxy]propanoic acid ion, 4,7,10,13-tetraoxatetradecanoic acid ion, 4,7,10,13-tetraoxapentadecanoic acid ion, 4,7,10,13,16-pentaoxaheptadecanoic acid ion, 4,7,10,13,16-pentaoxaoctadecanoic acid ion, (methylthio)acetic acid ion, (ethylthio)acetic acid ion, 3-(methylthio)propanoic acid ion, 3-[(2-methoxyethyl)thio]propanoic acid ion, and 3-[(2-ethoxyethyl)thio]propanoic acid ion. Preferred examples thereof include methoxyacetic acid ion, 3-(2-methoxyethoxy)propanoic acid ion, 3-(2-ethoxyethoxy)propanoic acid ion, 3-[2-(2-methoxyethoxy)ethoxy]propanoic acid ion, 3-[2-(2-ethoxyethoxy)ethoxy]propanoic acid ion, and 4,7,10,13-tetraoxatetradecanoic acid ion, and particularly preferred examples thereof include methoxyacetic acid ion, 3-(2-methoxyethoxy)propanoic acid ion, 3-(2-ethoxyethoxy)propanoic acid ion, and 3-(methylthio)propanoic acid ion.

In Formula (2), $Z^+$ represents a nitrogen ion or a phosphorus ion. $R^2$ to $R^5$ represent a hydrocarbon group having 1 to 20 carbon atoms which may contain a hetero atom, preferably a hydrocarbon group having 1 to 12 carbon atoms which may contain a hetero atom, and more preferably a hydrocarbon group having 1 to 10 carbon atoms which may contain a hetero atom. Even more preferably, at least one of $R^2$ to $R^5$ is an alkoxyalkyl group.

Specific examples of the onium cation represented by Formula (2) include tetramethylammonium, tetraethylammonium, tetrapropylammonium, tetrabutylammonium, tetrapentylammonium, tetrahexylammonium, tetraheptylammonium, tetraoctylammonium, tetranonylammonium, tetra(decyl)ammonium, N-ethyl-N,N,N-trimethylammonium, N,N,N-trimethyl-N-propylammonium, N-butyl-N,N,N-trimethylammonium, N,N,N-triethyl-N-decylammonium, N,N,N-triethyl-N-eicosylammonium, N,N,N-tributyl-N-pentylammonium, N,N,N-tributyl-N-hexylammonium, N,N,N-tributyl-N-heptylammonium, N,N,N-tributyl-N-octylammonium, N,N,N-tributyl-N-nonylammonium, N,N,N-tributyl-N-decylammonium, N,N,N-tributyl-N-eicosylammonium, N,N-diethyl-N-methyl-N-propylammonium, N-butyl-N,N-diethyl-N-methylammonium, N,N,N-trimethyl-N-(2-methoxyethyl)ammonium, N,N-diethyl-N-(2-methoxyethyl)-N-methylammonium, N,N,N-triethyl-N-(2-ethoxyethyl)ammonium, N,N-diethyl-N-propyl-N-(2-ethoxyethyl)ammonium, N-ethyl-N-[2-(2-methoxyethoxy)ethyl]-N,N-dimethylammonium, N,N-diethyl-N-[2-(2-methoxyethoxy)ethyl]-N-methylammonium, N,N-di(2-methoxyethyl)-N,N-dimethylammonium, N,N-di(2-ethoxyethyl)-N,N-dimethylammonium, N-[2-(2-methoxyethoxy)ethyl]-N-(2- methoxyethyl)-N,N-dimethylammonium, N-(2-ethoxyethyl)-N-[2-(2-methoxyethoxy)ethyl]-N,N-dimethylammonium, tetramethylphosphonium, tetraethylphosphonium, tetrapropylphosphonium, tetrabutylphosphonium, tetrapentylphosphonium, tetrahexylphosphonium, tetraheptylphosphonium, tetraoctylphosphonium, tetranonylphosphonium, tetra(decyl)phosphonium, P,P,P-tributyl-P-octylphosphonium, tributyldodecylphosphonium, tetradecylphosphonium, P,P,P-trimethyl-P-(2-methoxyethyl)phosphonium, P,P-diethyl-P-(2-methoxyethyl)-P-methylphosphonium, P,P,P-triethyl-P-(2-ethoxyethyl)phosphonium, P,P-diethyl-P-propyl-P-(2-ethoxyethyl)phosphonium, P-ethyl-P-[2-(2-methoxyethoxy)ethyl]-P,P-dimethylphosphonium, P,P-diethyl-P-[2-(2-methoxyethoxy)ethyl]-P-methylphosphonium, P,P-di(2-methoxyethyl)-P,P-dimethylphosphonium, P,P-di(2-ethoxyethyl)-P,P-dimethylphosphonium, P-[2-(2-methoxyethoxy)ethyl]-P-(2-methoxyethyl)-P,P-dimethylphosphonium, and P-(2-ethoxyethyl)-P-[2-(2-methoxyethoxy)ethyl]-P,P-dimethylphosphonium. Preferred examples thereof include N,N,N-trimethyl-N-propylammonium, N-butyl-N,N-diethyl-N-methylammonium, N,N-diethyl-N-(2-methoxyethyl)-N-methylammonium, N-ethyl-N-[2-(2-methoxyethoxy)ethyl]-N,N-dimethylammonium, N,N,N-trimethyl-N-(2-ethoxymethyl)ammonium, and N,N,N-triethyl-N-(2-ethoxyethyl)ammonium, and particularly preferred examples thereof include N,N-diethyl-N-(2-methoxyethyl)-N-methylammonium and N-ethyl-N-[2-(2-methoxyethoxy)ethyl]-N,N-dimethylammonium, but the present invention is not limited to them.

In Formula (3), $R^6$ represents a hydrocarbon group having 4 to 20 carbon atoms which may contain a hetero atom, preferably a hydrocarbon group having 4 to 10 carbons, and particularly preferably a hydrocarbon group having 4 to 7 carbons. When $R^6$ is a hydrocarbon group having 4 to 20 carbon atoms which contains a hetero atom, the hetero atom is preferably an oxygen atom. $R^7$ and $R^8$ represent a hydrocarbon group having 1 to 20 carbon atoms which may contain a hetero atom, preferably a hydrocarbon group having 1 to 12 carbons which may contain a hetero atom, and particularly preferably a hydrocarbon group having 1 to 10 carbons which may contain a hetero atom, with the proviso that $R^8$ does not exist when the nitrogen ion has a double bond. It is more preferable that at least one of $R^7$ and $R^8$ is a hydrocarbon group having 1 to 20 carbon atoms which contains a hetero atom, and at least one of $R^7$ and $R^8$ is an alkoxyalkyl group. But $R^7$ and $R^8$ are preferably a hydrocarbon group having 1 to 6 carbon atoms when $R^6$ is a hydrocarbon group having 4 to 20 carbon atoms which contains a hetero atom.

Examples of the onium cation represented by Formula (3) include pyrrolidinium cation, piperidinium cation, morpholinium cation, pyridinium cation, and pyrimidinium cation. Preferred examples thereof include pyrrolidinium cation, piperidinium cation, and morpholinium cation. Particularly preferred examples include morpholinium cation.

Specific examples of the onium cation represented by Formula (3) include 1,1-dimethylpyrrolidinium, 1-ethyl-1-methylpyrrolidinium, 1-methyl-1-propylpyrrolidinium, 1-butyl-1-methylpyrrolidinium, 1-methyl-1-pentylpyrrolidinium, 1-hexyl-1-methylpyrrolidinium, 1-heptyl-1-methylpyrrolidinium, 1-methyl-1-nonylpyrrolidinium, 1-decyl-1-methylpyrrolidinium, 1-allyl-1-methylpyrrolidinium, 1-allyl-1-ethylpyrrolidinium, 1-(2-methoxyethyl)-1-methylpyrrolidinium, 1-(2-ethoxyethyl)-1-methylpyrrolidinium, 1,1-dimethylpiperidinium, 1-ethyl-1-methylpiperidinium, 1-methyl-1-propylpiperidinium, 1-butyl-1-methylpiperidinium, 1-methyl-1-pentylpiperidinium, 1-hexyl-1-methylpiperidinium, 1-heptyl-1-methylpiperidinium, 1-methyl-1-octylpiperidinium, 1-methyl-1-nonylpiperidinium, 1-decyl-1-methylpiperidinium, 1-allyl-1-methylpiperidinium, 1-allyl-1-ethylpiperidinium, 1-(2-methoxyethyl)-1-methylpiperidinium, 1-(2-ethoxyethyl)-1-methylpiperidinium, N,N-dimethylmorpholinium, N-ethyl-N-methylmorpholinium, N-methyl-N-propylmorpholinium, N-butyl-N-methylmorpholinium, N-methyl-N-pentylmorpholinium, N-hexyl-N-methylmorpholinium, N-heptyl-N-methylmorpholinium, N-methyl-N-octylmorpholinium, N-methyl-N-nonylmorpholinium, N-decyl-N-methylmorpholinium, N-allyl-N-methylmorpholinium, N-allyl-N-ethylmorpholinium, N-(2-methoxyethyl)-N-methylmorpholinium, N-(2-ethoxyethyl)-N-methylmorpholinium, 1-methylpyridinium, 1-ethylpyridinium, 1-propylpyridinium, 1-butylpyridinium, 1-pentylpyridinium, 1-hexylpyridinium, 1-heptylpyridinium, 1-octylpyridinium, 1-nonylpyridinium, 1-decylpyridinium, 1-allylpyridinium, 1-(2-methoxyethyl)pyridinium, and 1-(2-ethoxyethyl)pyridinium. It is preferably N-allyl-N-methylmorpholinium, but the present invention is not limited to them.

In Formula (4), $R^9$ represents a hydrocarbon group having 2 to 20 carbon atoms which may contain a hetero atom, preferably a hydrocarbon group having 2 to 12 carbons which may contain a hetero atom, and particularly preferably a hydrocarbon group having 2 to 10 carbons which may contain a hetero atom. $R^{10}$, $R^{11}$ and $R^{12}$ represent a hydrogen atom or a hydrocarbon group having 1 to 20 carbon atoms which may contain a hetero atom, preferably a hydrocarbon group having 1 to 12 carbons which may contain a hetero atom, and particularly preferably a hydrocarbon group having 1 to 10 carbons which may contain a hetero atom. At least one of $R^{10}$ to $R^{12}$ is preferably a hydrocarbon group which contains a hetero atom, and it is more preferable that at least one of $R^{10}$ to $R^{12}$ is an alkoxyalkyl group.

Specific examples of the onium cation represented by Formula (4) include 1,3-dimethylimidazolium, 1-ethyl-3-methylimidazolium, 1-methyl-3-propylimidazolium, 1-butyl-3-methylimidazolium, 1-methyl-3-pentylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-allyl-3-methylimidazolium, 1-allyl-3-ethylimidazolium, 1-(2-methoxyethyl)-3-methylimidazolium, 1-(2-ethoxyethyl)-3-methylimidazolium, 1-ethyl-3-(2-methoxyethyl)imidazolium, and 1-ethyl-3-(2-ethoxyethyl)imidazolium, preferred examples thereof include 1-ethyl-3-methylimidazolium, 1-butyl-3-methylimidazolium, 1-(2-methoxyethyl)-3-methylimidazolium, 1-(2-ethoxyethyl)-3-methylimidazolium, 1-ethyl-3-(2-methoxyethyl)imidazolium, and 1-ethyl-3-(2-ethoxyethyl)imidazolium, and particularly preferred examples thereof include 1-ethyl-3-methylimidazolium and 1-butyl-3-methylimidazolium, but the present invention is not limited to them.

Specific examples of the onium salt (1) include tetramethylammonium methoxyacetate, tetraethylammonium methoxyacetate, tetrapropylammonium methoxyacetate, tetrabutylammonium methoxyacetate, N-ethyl-N,N,N-trimethylammonium methoxyacetate, N,N,N-trimethyl-N-propylammonium methoxyacetate, N-butyl-N,N,N-trimethylammonium methoxyacetate, N,N-diethyl-N-methyl-N-propylammonium methoxyacetate, N-butyl-N,N-diethyl-N-methylammonium methoxyacetate, tetramethylammonium 3-(2-methoxyethoxy)propanoate, tetraethylammonium 3-(2-methoxyethoxy)propanoate, tetrapropylammonium 3-(2-methoxyethoxy)propanoate, tetrabutylammonium 3-(2-methoxyethoxy)propanoate, N-ethyl-N,N,N-trimethylammonium 3-(2-methoxyethoxy)propanoate, N,N,N-trimethyl-N-propylammonium 3-(2-methoxyethoxy)propanoate, N-butyl-N,N,N-trimethylammonium 3-(2-methoxyethoxy)propanoate, N,N-diethyl-N-methyl-N-propylammonium 3-(2-methoxyethoxy)propanoate, N-butyl-N,N-diethyl-N-methylammonium 3-(2-methoxyethoxy)propanoate, tetramethylammonium 3-(2-ethoxyethoxy)propanoate, tetraethylammonium 3-(2-ethoxyethoxy)propanoate, tetrapropylammonium 3-(2-ethoxyethoxy)propanoate, tetrabutylammonium 3-(2-ethoxyethoxy)propanoate, N-ethyl-N,N,N-trimethylammonium 3-(2-ethoxyethoxy)propanoate, N,N,N-trimethyl-N-propylammonium 3-(2-ethoxyethoxy)propanoate, N-butyl-N,N,N-trimethylammonium 3-(2-ethoxyethoxy)propanoate, N,N-diethyl-N-methyl-N-propylammonium 3-(2-ethoxyethoxy)propanoate, N-butyl-N,N-diethyl-N-methylammonium 3-(2-ethoxyethoxy)propanoate, tetramethylammonium 3-[2-(2-methoxyethoxy)ethoxy]propanoate, tetraethylammonium 3-[2-(2-methoxyethoxy)ethoxy]propanoate, tetrapropylammonium 3-[2-(2-methoxyethoxy)ethoxy]propanoate, tetrabutylammonium 3-[2-(2-methoxyethoxy)ethoxy]propanoate, N-ethyl-N,N,N-trimethylammonium 3-[2-(2-methoxyethoxy)ethoxy]propanoate, N,N,N-trimethyl-N-propylammonium 3-[2-(2-methoxyethoxy)ethoxy]propanoate, N-butyl-N,N,N-trimethylammonium 3-[2-(2-methoxyethoxy)ethoxy]propanoate, N,N-diethyl-N-methyl-N-propylammonium 3-methoxyethoxy)ethoxy]propanoate, N-butyl-N,N-diethyl-N-methylammonium 3-[2-(2-methoxyethoxy)ethoxy]propanoate, tetramethylammonium 4,7,10,13-tetraoxatetradecanoate, tetraethylammonium 4,7,10,13-tetraoxatetradecanoate, tetrapropylammonium 4,7,10,13-tetraoxatetradecanoate, tetrabutylammonium 4,7,10,13-tetraoxatetradecanoate, N-ethyl-N,N,N-trimethylammonium 4,7,10,13-tetraoxatetradecanoate, N,N,N-trimethyl-N-propylammonium 4,7,10,13-tetraoxatetradecanoate, N-butyl-N,N,N-trimethylammonium 4,7,10,13-tetraoxatetradecanoate, N,N-diethyl-N-methyl-N-propylammonium 4,7,10,13-tetraoxatetradecanoate, N-butyl-N,N-diethyl-N-methylammonium 4,7,10,13-tetraoxatetradecanoate, tetramethylammonium 3-(methylthio)propanoate, tetraethylammonium 3-(methylthio)propanoate, tetrapropylammonium 3-(methylthio)propanoate, tetrabutylammonium 3-(methylthio)propanoate, N-ethyl-N,N,N-trimethylammonium 3-(methylthio)propanoate, N,N,N-trimethyl-N-propylammonium 3-(methylthio)propanoate, N-butyl-N,N,N-trimethylammonium 3-(methylthio)propanoate, N,N-diethyl-N-methyl-N-propylammonium 3-(methylthio)propanoate, N-butyl-N,N-diethyl-N-methylammonium 3-(methylthio)propanoate, N,N,N-trimethyl-N-(2-methoxyethyl)ammonium methoxyacetate, N,N-diethyl-N-(2-methoxyethyl)-N-methylammonium methoxyacetate, N,N,N-triethyl-N-(2-ethoxyethyl)ammonium methoxyacetate, N,N-diethyl-N-propyl-N-(2-ethoxyethyl)ammonium methoxyacetate, N-ethyl-N-[2-(2-methoxyethoxy)ethyl]-N,N-dimethylammonium methoxyacetate, N,N-diethyl-N-[2-(2-methoxyethoxy)ethyl]-N-methylammonium methoxyacetate, N,N-di(2-methoxyethyl)-N,N-dimethylammonium methoxyacetate, N,N-di(2-ethoxyethyl)-N,N-dimethylammonium methoxyacetate, N-[2-(2-methoxyethoxy)ethyl]-N-(2-methoxyethyl)-N,N-dimethylammonium methoxyacetate, N-(2-ethoxyethyl)-N-[2-(2-methoxyethoxy)ethyl]-N,N-dimethylammonium methoxyacetate, N,N,N-trimethyl-N-(2-methoxyethyl)ammonium 3-(2-methoxyethoxy)propanoate, N,N-diethyl-N-(2-methoxyethyl)-N-methylammonium 3-(2-methoxyethoxy)propanoate, N,N,N-triethyl-N-(2-ethoxyethyl) ammonium 3-(2-methoxyethoxy)propanoate, N,N-diethyl-N-propyl-N-(2-ethoxyethyl)ammonium 3-(2-methoxyethoxy)propanoate, N-ethyl-N-[2-(2-methoxyethoxy) ethyl]-N,N-dimethylammonium 3-(2-methoxyethoxy)propanoate, N,N-diethyl-N-[2-(2-methoxyethoxy)ethyl]-N-methyl ammonium 3-(2-methoxyethoxy)propanoate, N,N-di(2-methoxyethyl)-N,N-dimethylammonium 3-(2-methoxyethoxy)propanoate, N,N-di (2-ethoxyethyl)-N,N-dimethylammonium 3-(2-methoxyethoxy)propanoate, N-[2-(2-methoxyethoxy)ethyl]-N-(2-methoxyethyl)-N,N-dimethylammonium 3-(2-methoxyethoxy)propanoate, N-(2-ethoxyethyl)-N-[2-(2-methoxyethoxy)ethyl]-N,N-dimethylammonium 3-(2-methoxyethoxy)propanoate, N,N,N-trimethyl-N-(2-methoxyethyl)ammonium 3 (2-ethoxyethoxy)propanoate, N,N-diethyl-N-(2-methoxyethyl)-N-methylammonium 3-(2-ethoxyethoxy)propanoate, N,N,N-triethyl-N-(2-ethoxyethyl)ammonium 3-(2-ethoxyethoxy)propanoate, N,N-diethyl-N-propyl-N-(2-ethoxyethyl)ammonium 3-(2-ethoxyethoxy)propanoate, N-ethyl-N-[2-(2-methoxyethoxy)ethyl]-N,N-dimethylammonium 3-(2-ethoxyethoxy)propanoate, N,N-diethyl-N-[2-(2-methoxyethoxy)ethyl]-N-methylammonium 3-(2-ethoxyethoxy)propanoate, N,N-di(2-methoxyethyl)-N,N-dimethylammonium 3-(2-ethoxyethoxy)propanoate, N,N-di(2-ethoxyethyl)-N,N-dimethylammonium 3-(2-ethoxyethoxy)propanoate, N-[2-(2-methoxyethoxy)ethyl]-N-(2-methoxyethyl)-N,N-dimethylammonium 3-(2-ethoxyethoxy)propanoate, N-(2-ethoxyethyl)-N-[2-(2-methoxyethoxy)ethyl]-N,N-dimethylammonium 3-(2-ethoxyethoxy)propanoate, N,N,N-trimethyl-N-(2-m ethoxyethyl) ammonium 3-[2-(2-methoxyethoxy)ethoxy]propanoate, N,N-diethyl-N-(2-methoxyethyl)-N-methylammonium 3-[2-(2-methoxyethoxy)ethoxy]propanoate, N,N,N-triethyl-N-(2-ethoxyethyl)ammonium 3-[2-(2-methoxyethoxy)ethoxy]propanoate, N,N-diethyl-N-propyl-N-(2-ethoxyethyl) ammonium 3-[2-(2-methoxyethoxy)ethoxy]propanoate, N-ethyl-N-[2-(2-methoxyethoxy)ethyl]-N,N-dimethylammonium 3-[2-(2-methoxyethoxy)ethoxy]propanoate, N,N-diethyl-N-[2-(2-methoxyethoxy)ethyl]-N-methylammonium 3-[2-(2-methoxyethoxy)ethoxy]propanoate, N,N-di(2-methoxyethyl)-N,N-dimethylammonium 3-[2-(2-methoxyethoxy)ethoxy]propanoate, N,N-di(2-ethoxyethyl)-N,N-dimethylammonium 3-[2-(2-methoxyethoxy)ethoxy]propanoate, N-[2-(2-methoxyethoxy)ethyl]-N-(2-methoxyethyl)-N,N-dimethylammonium 3-[2-(2-methoxyethoxy)ethoxy]propanoate, N-(2-ethoxyethyl)-N-[2-(2-methoxyethoxy)ethyl]-N,N-dimethylammonium 3-[2-(2-methoxyethoxy)ethoxy]propanoate, N,N,N-trimethyl-N-(2-methoxyethyl)ammonium 4,7,10,13-tetraoxatetradecanoate, N,N-diethyl-N-(2-methoxyethyl)-N-methylammonium 4,7,10,13-tetraoxatetradecanoate, N,N,N-triethyl-N-(2-ethoxyethyl)ammonium 4,7,10,13-tetraoxatetradecanoate, N,N-diethyl-N-propyl-N-(2-ethoxyethyl)ammonium 4,7,10,13-tetraoxatetradecanoate, N-ethyl-N-[2-(2-methoxyethoxy)ethyl]-N,N-dimethylammonium 4,7,10,13-tetraoxatetradecanoate, N,N-diethyl-N-[2-(2-methoxyethoxy)ethyl]-N-methylammonium 4,7,10,13-tetraoxatetradecanoate, N,N-di(2-methoxyethyl)-N,N-dimethylammonium 4,7,10,13-tetraoxatetradecanoate, N,N-di(2-ethoxyethyl)-N,N-dimethylammonium 4,7,10,13-tetraoxatetradecanoate, N-[2-(2-methoxyethoxy)ethyl]-N-(2-methoxyethyl)-N,N-dimethylammonium 4,7,10,13- tetraoxatetradecanoate, N-(2-ethoxyethyl)-N-[2-(2-methoxyethoxy)ethyl]-N,N-dimethylammonium 4,7,10,13-tetraoxatetradecanoate,
N,N,N-trimethyl-N-(2-methoxyethyl)ammonium 3-(methylthio)propanoate, N,N-diethyl-N-(2-methoxyethyl)-N-methylammonium 3-(methylthio)propanoate, N,N,N-triethyl-N-(2-ethoxyethyl)ammonium 3-(methylthio)propanoate, N,N-diethyl-N-propyl-N-(2-ethoxyethyl)ammonium 3-(methylthio)propanoate, N-ethyl-N-[2-(2-methoxyethoxy)ethyl]-N,N-dimethylammonium 3-(methylthio)propanoate, N,N-diethyl-N-[2-(2-methoxyethoxy)ethyl]-N-methylammonium 3-(methylthio)propanoate, N,N-di(2-methoxyethyl)-N,N-dimethylammonium 3-(methylthio)propanoate, N,N-di(2-ethoxyethyl)-N,N-dimethylammonium 3-(methylthio)propanoate, N-[2-(2-methoxyethoxy)ethyl]-N-(2-methoxyethyl)-N,N-dimethylammonium 3-(methylthio)propanoate, N-(2-ethoxyethyl)-N-[2-(2-methoxyethoxy)ethyl]-N,N-dimethylammonium 3-(methylthio)propanoate, tetramethylphosphonium methoxyacetate, tetraethylphosphonium methoxyacetate, tetrapropylphosphonium methoxyacetate, tetrabutylphosphonium methoxyacetate, P,P,P-trimethyl-P-(2-methoxyethyl)phosphonium methoxyacetate, P,P-diethyl-P-(2-methoxyethyl)-P-methylphosphonium methoxyacetate, P,P,P-triethyl-P-(2-ethoxyethyl)phosphonium methoxyacetate, P,P-diethyl-P-propyl-P-(2-ethoxyethyl)phosphonium methoxyacetate, P-ethyl-P-[2-(2-methoxyethoxy)ethyl]-P,P-dimethylphosphonium methoxyacetate, P,P-diethyl-P-[2-(2-methoxyethoxy)ethyl]-P-methylphosphonium methoxyacetate, P,P-di(2-methoxyethyl)-P,P-dimethylphosphonium methoxyacetate, P,P-di(2-ethoxyethyl)-P,P-dimethylphosphonium methoxyacetate, P-[2-(2-methoxyethoxy)ethyl]-P-(2-methoxyethyl)-P,P-dimethylphosphonium methoxyacetate, P-(2-ethoxyethyl)-P-[2-(2-methoxyethoxy)ethyl]-P,P-dimethylphosphonium methoxyacetate, tetramethylphosphonium 3-(2-methoxyethoxy)propanoate, tetraethylphosphonium 3-(2-methoxyethoxy)propanoate, tetrapropylphosphonium 3-(2-methoxyethoxy)propanoate, tetrabutylphosphonium 3-(2-methoxyethoxy)propanoate, P,P,P-trimethyl-P-(2-methoxyethyl)phosphonium 3-(2-methoxyethoxy)propanoate, P,P-diethyl-P-(2-methoxyethyl)-P-methylphosphonium 3-(2-methoxyethoxy)propanoate, P,P,P-triethyl-P-(2-ethoxyethyl)phosphonium 3-(2-methoxyethoxy)propanoate, P,P-diethyl-P-propyl-P-(2-ethoxyethyl)phosphonium 3-(2-methoxyethoxy)propanoate, P-ethyl-P-[2-(2-methoxyethoxy)ethyl]-P,P-dimethylphosphonium 3-(2-methoxyethoxy)propanoate, P,P-diethyl-P-[2-(2-methoxyethoxy)ethyl]-P-methylphosphonium 3-(2-methoxyethoxy)propanoate, P,P-di(2-methoxyethyl)-P,P-dimethylphosphonium 3-(2-methoxyethoxy)propanoate, P,P-di(2-ethoxyethyl)-P,P-dimethylphosphonium 3-(2-methoxyethoxy)propanoate, P-[2-(2-methoxyethoxy)ethyl]-P-(2-methoxyethyl)-P,P-dimethylphosphonium 3-(2-methoxyethoxy)propanoate, P-(2-ethoxyethyl)-P-[2-(2-methoxyethoxy)ethyl]-P,P-dimethylphosphonium 3-(2-methoxyethoxy)propanoate, tetramethylphosphonium 3-(2-ethoxyethoxy)propanoate, tetraethylphosphonium 3-(2-ethoxyethoxy)propanoate, tetrapropylphosphonium 3-(2-ethoxyethoxy)propanoate, tetrabutylphosphonium 3-(2-ethoxyethoxy)propanoate, P,P,P-trimethyl-P-(2-methoxyethyl)phosphonium 3-(2-ethoxyethoxy)propanoate, P,P-diethyl-P-(2-methoxyethyl)-P-methylphosphonium 3-(2-ethoxyethoxy)propanoate, P,P,P-triethyl-P-(2-ethoxyethyl)phosphonium 3-(2-ethoxyethoxy)propanoate, P,P-diethyl-P-propyl-P-(2-ethoxyethyl)phosphonium 3-(2-ethoxyethoxy)propanoate, P-ethyl-P-[2-(2-methoxyethoxy)ethyl]-P,P-dimethylphosphonium 3-(2-ethoxyethoxy)propanoate, P,P-diethyl-P-[2-(2-methoxyethoxy)ethyl]-P-methylphosphonium 3-(2-ethoxyethoxy)propanoate, P,P-di(2-methoxyethyl)-P,P-dimethylphosphonium 3-(2-ethoxyethoxy)propanoate, P,P-di(2-ethoxyethyl)-P,P-dimethylphosphonium 3-(2-ethoxyethoxy)propanoate, P-[2-(2-methoxyethoxy)ethyl]-P-(2-methoxyethyl)-P,P-dimethylphosphonium 3-(2-ethoxyethoxy)propanoate, P-(2-ethoxyethyl)-P-[2-(2-methoxyethoxy)ethyl]-P,P-dimethylphosphonium 3-(2-ethoxyethoxy)propanoate, tetramethylphosphonium 3-[2-(2-methoxyethoxy)ethoxy]propanoate, tetraethylphosphonium 3-[2-(2-methoxyethoxy)ethoxy]propanoate, tetrapropylphosphonium 3-[2-(2-methoxyethoxy)ethoxy]propanoate, tetrabutylphosphonium 3-[2-(2-methoxyethoxy)ethoxy]propanoate, P,P,P-trimethyl-P-(2-methoxyethyl)phosphonium 3-[2-(2-methoxyethoxy)ethoxy]propanoate, P,P-diethyl-P-(2-methoxyethyl)-P-methylphosphonium 3-[2-(2-methoxyethoxy)ethoxy]propanoate, P,P,P-triethyl-P-(2-ethoxyethyl)phosphonium 3-[2-(2-methoxyethoxy)ethoxy]propanoate, P,P-diethyl-P-propyl-P-(2-ethoxyethyl)phosphonium 3-[2-(2-methoxyethoxy)ethoxy]propanoate, P-ethyl-P-[2-(2-methoxyethoxy)ethyl]-P,P-dimethylphosphonium 3-[2-(2-methoxyethoxy)ethoxy]propanoate, P,P-diethyl-P-[2-(2-methoxyethoxy)ethyl]-P-methylphosphonium 3-[2-(2-methoxyethoxy)ethoxy]propanoate, P,P-di(2-methoxyethyl)-P,P-dimethylphosphonium 3-[2-(2-methoxyethoxy)ethoxy]propanoate, P,P-di(2-ethoxyethyl)-P,P-dimethylphosphonium 3-[2-(2-methoxyethoxy)ethoxy]propanoate, P-[2-(2-methoxyethoxy)ethyl]-P-(2-methoxyethyl)-P,P-dimethylphosphonium 3-[2-(2-methoxyethoxy)ethoxy]propanoate, P-(2-ethoxyethyl)-P-[2-(2-methoxyethoxy)ethyl]-P,P-dimethylphosphonium 3-[2-(2-methoxyethoxy)ethoxy]propanoate, tetramethylphosphonium 4,7,10,13-tetraoxatetradecanoate, tetraethylphosphonium 4,7,10,13-tetraoxatetradecanoate, tetrapropylphosphonium 4,7,10,13-tetraoxatetradecanoate, tetrabutylphosphonium 4,7,10,13-tetraoxatetradecanoate, P,P,P-trimethyl-P-(2-methoxyethyl)phosphonium 4,7,10,13-tetraoxatetradecanoate, P,P-diethyl-P-(2-methoxyethyl)-P-methylphosphonium 4,7,10,13-tetraoxatetradecanoate, P,P,P-triethyl-P-(2-ethoxyethyl)phosphonium 4,7,10,13-tetraoxatetradecanoate, P,P-diethyl-P-propyl-P-(2-ethoxyethyl)phosphonium 4,7,10,13-tetraoxatetradecanoate, P-ethyl-P-[2-(2-methoxyethoxy)ethyl]-P,P-dimethylphosphonium 4,7,10,13-tetraoxatetradecanoate, P,P-diethyl-P-[2-(2-methoxyethoxy)ethyl]-P-methylphosphonium 4,7,10,13-tetraoxatetradecanoate, P,P-di(2-methoxyethyl)-P,P-dimethylphosphonium 4,7,10,13-tetraoxatetradecanoate, P,P-di(2-ethoxyethyl)-P,P-dimethylphosphonium 4,7,10,13-tetraoxatetradecanoate, P-[2-(2-methoxyethoxy)ethyl]-P-(2-methoxyethyl)-P,P-dimethylphosphonium 4,7,10,13-tetraoxatetradecanoate, P-(2-ethoxyethyl)-P-[2-(2-methoxyethoxy)ethyl]-P,P-dimethylphosphonium 4,7,10,13-tetraoxatetradecanoate, tetramethylphosphonium 3-(methylthio)propanoate, tetraethylphosphonium 3-(methylthio)propanoate, tetrapropylphosphonium 3-(methylthio)propanoate, tetrabutylphosphonium 3-(methylthio)propanoate, P,P,P-trimethyl-P-(2-methoxyethyl)phosphonium 3-(methylthio)propanoate, P,P-diethyl-P-(2-methoxyethyl)-P-methylphosphonium 3-(methylthio)propanoate, P,P,P-triethyl-P-(2-ethoxyethyl)phosphonium 3-(methylthio)propanoate, P,P-diethyl-P-propyl-P-(2-ethoxyethyl)phosphonium 3-(methylthio)propanoate, P-ethyl-P-[2-(2-methoxyethoxy)ethyl]-P,P-dimethylphosphonium 3-(methylthio)propanoate, P,P-diethyl-P-[2-(2-methoxyethoxy)ethyl]-P-methylphosphonium 3-(methylthio)propanoate, P,P-di(2-methylthio)-P,P-dimethylphosphonium 3-(methylthio)propanoate, P,P-di(2-ethoxyethyl)-P,P-dimethylphosphonium 3-(methylthio)propanoate, P-[2-(2-methoxyethoxy)ethyl]-P-(2-methoxyethyl)-P,P-dimethylphosphonium 3-(methylthio)propanoate, P-(2-ethoxyethyl)-P-[2-(2-methoxyethoxy)ethyl]-P,P-dimethylphosphonium 3-(methylthio)propanoate, 1,1-dimethylpyrrolidinium methoxyacetate, 1-ethyl-1-methylpyrrolidinium methoxyacetate, 1-methyl-1-propylpyrrolidinium methoxyacetate, 1-butyl-1-methylpyrrolidinium methoxyacetate, 1-allyl-1-methylpyrrolidinium methoxyacetate, 1-allyl-1-ethylpyrrolidinium methoxyacetate, 1-(2-methoxyethyl)-1-methylpyrrolidinium methoxyacetate, 1-(2-ethoxyethyl)-1-methylpyrrolidinium methoxyacetate, 1,1-dimethylpyrrolidinium 3-(2-methoxyethoxy)propanoate, 1-ethyl-1-methylpyrrolidinium 3-(2-methoxyethoxy)propanoate, 1-methyl-1-propylpyrrolidinium 3-(2-methoxyethoxy)propanoate, 1-butyl-1-methylpyrrolidinium 3-(2-methoxyethoxy)propanoate, 1-allyl-1-methylpyrrolidinium 3-(2-methoxyethoxy)propanoate, 1-allyl-1-ethylpyrrolidinium 3-(2-methoxyethoxy)propanoate, 1-(2-methoxyethyl)-1-methylpyrrolidinium 3-(2-methoxyethoxy)propanoate, 1-(2-ethoxyethyl)-1-methylpyrrolidinium 3-(2-methoxyethoxy)propanoate, 1,1-dimethylpyrrolidinium 3-(2-ethoxyethoxy)propanoate, 1-ethyl-1-methylpyrrolidinium 3-(2-ethoxyethoxy)propanoate, 1-methyl-1-propylpyrrolidinium 3-(2-ethoxyethoxy)propanoate, 1-butyl-1-methylpyrrolidinium 3-(2-ethoxyethoxy)propanoate, 1-allyl-1-methylpyrrolidinium 3-(2-ethoxyethoxy)propanoate, 1-allyl-1-ethylpyrrolidinium 3-(2-ethoxyethoxy)propanoate, 1-(2-methoxyethyl)-1-methylpyrrolidinium 3-(2-ethoxyethoxy)propanoate, 1-(2-ethoxyethyl)-1-methylpyrrolidinium 3-(2-ethoxyethoxy)propanoate, 1,1-dimethylpyrrolidinium 3-[2-(2-methoxyethoxy)ethoxy]propanoate, 1-ethyl-1-methylpyrrolidinium 3-[2-(2-methoxyethoxy)ethoxy]propanoate, 1-methyl-1-propylpyrrolidinium 3-[2-(2-methoxyethoxy)ethoxy]propanoate, 1-butyl-1-methylpyrrolidinium 3-[2-(2-methoxyethoxy)ethoxy]propanoate, 1-allyl-1-methylpyrrolidinium 3-[2-(2-methoxyethoxy)ethoxy]propanoate, 1-allyl-1-ethylpyrrolidinium 3-[2-(2-methoxyethoxy)ethoxyl]propanoate, 1-(2-methoxyethyl)-1-methylpyrrolidinium 3-[2-(2-methoxyethoxy)ethoxy]propanoate, 1-(2-ethoxyethyl)-1-methylpyrrolidinium 3-[2-(2-methoxyethoxy)ethoxy]propanoate, 1,1-dimethylpyrrolidinium 4,7,10,13-tetraoxatetradecanoate, 1-ethyl-1-methylpyrrolidinium 4,7,10,13-tetraoxatetradecanoate, 1-methyl-1-propylpyrrolidinium 4,7,10,13-tetraoxatetradecanoate, 1-butyl-1-methylpyrrolidinium 4,7,10,13-tetraoxatetradecanoate, 1-allyl-1-methylpyrrolidinium 4,7,10,13-tetraoxatetradecanoate, 1-allyl-1-ethylpyrrolidinium 4,7,10,13-tetraoxatetradecanoate, 1-(2-methoxyethyl)-1-methylpyrrolidinium 4,7,10,13-tetraoxatetradecanoate, 1-(2-ethoxyethyl)-1-methylpyrrolidinium 4,7,10,13-tetraoxatetradecanoate, 1,1-dimethylpyrrolidinium 3-(methylthio)propanoate, 1-ethyl-1-methylpyrrolidinium 3-(methylthio)propanoate, 1-methyl-1-propylpyrrolidinium 3-(methylthio)propanoate, 1-butyl-1-methylpyrrolidinium 3-(methylthio)propanoate, 1-allyl-1-methylpyrrolidinium 3-(methylthio)propanoate, 1-allyl-1-ethylpyrrolidinium 3-(methylthio)propanoate, 1-(2-methoxyethyl)-1-methylpyrrolidinium 3-(methylthio)propanoate, 1-(2-ethoxyethyl)-1-methylpyrrolidinium 3-(methylthio)propanoate, 1,1-dimethylpiperidinium methoxyacetate, 1-ethyl-1-methylpiperidinium methoxyacetate, 1-methyl-1-propylpiperidinium methoxyacetate, 1-butyl-1-methylpiperidinium methoxyacetate, 1-allyl-1-methylpiperidinium methoxyacetate, 1-allyl-1-ethylpiperidinium methoxyacetate, 1-(2-methoxyethyl)-1-methylpiperidinium methoxyacetate, 1-(2-ethoxyethyl)-1-methylpiperidinium methoxyacetate, 1,1-dimethylpiperidinium 3(2-methoxyethoxy)propanoate, 1-ethyl-1-methylpiperidinium 3-(2-methoxyethoxy)propanoate, 1-methyl-1-propylpiperidinium 3-(2-methoxyethoxy)propanoate, 1-butyl-1-methylpiperidinium 3-(2-methoxyethoxy)propanoate, 1-allyl-1-methylpiperidinium 3-(2-methoxyethoxy)propanoate, 1-allyl-1-ethylpiperidinium 3-(2-methoxyethoxy)propanoate 1-(2-methoxyethyl)-1-methylpiperidinium 3-(2-methoxyethoxy)propanoate, 1-(2-ethoxyethyl)-1-methylpiperidinium 3-(2-methoxyethoxy)propanoate, 1,1-dimethylpiperidinium 3-(2-ethoxyethoxy)propanoate, 1-ethyl-1-methylpiperidinium 3-(2-ethoxyethoxy)propanoate, 1-methyl-1-propylpiperidinium 3-(2-ethoxyethoxy)propanoate, 1-butyl-1-methylpiperidinium 3-(2-ethoxyethoxy)propanoate, 1-allyl-1-methylpiperidinium 3-(2-ethoxyethoxy)propanoate, 1-allyl-1-ethylpiperidinium 3-(2-ethoxyethoxy)propanoate, 1-(2-methoxyethyl)-1-methylpiperidinium 3-(2-ethoxyethoxy)propanoate, 1-(2-ethoxyethyl)-1-methylpiperidinium 3-(2-ethoxyethoxy)propanoate, 1,1-dimethylpiperidinium 3-[2-(2-methoxyethoxy)ethoxy]propanoate, 1-ethyl-1-methylpiperidinium 3-[2-(2-methoxyethoxy)ethoxy]propanoate, 1-methyl-1-propylpiperidinium 3-[2-(2-methoxyethoxy)ethoxy]propanoate, 1-butyl-1-methylpiperidinium 3-[2-(2-methoxyethoxy)ethoxy]propanoate, 1-allyl-1-methylpiperidinium 3-[2-(2-methoxyethoxy)ethoxy]propanoate, 1-allyl-1-ethylpiperidinium 3-[2-(2-methoxyethoxy)ethoxy]propanoate, 1-(2-methoxyethyl)-1-methylpiperidinium 3-[2-(2methoxyethoxy)ethoxy]propanoate, 1-(2-ethoxyethyl)-1-methylpiperidinium 3-[2-(2-methoxyethoxy)ethoxy]propanoate, 1,1-dimethylpiperidinium 4,7,10,13-tetraoxatetradecanoate, 1-ethyl-1-methylpiperidinium 4,7,10,13-tetraoxatetradecanoate, 1-methyl-1-propylpiperidinium 4,7,10,13-tetraoxatetradecanoate, 1-butyl-1-methylpiperidinium 4,7,10,13-tetraoxatetradecanoate, 1-allyl-1-methylpiperidinium 4,7,10,13-tetraoxatetradecanoate, 1-allyl-1-ethylpiperidinium 4,7,10,13-tetraoxatetradecanoate, 1-(2-methoxyethyl)-1-methylpiperidinium 4,7,10,13-tetraoxatetradecanoate, 1-(2-ethoxyethyl)-1-methylpiperidinium 4,7,10,13-tetraoxatetradecanoate, 1,1-dimethylpiperidinium 3-(methylthio)propanoate, 1-ethyl-1-methylpiperidinium 3-(methylthio)propanoate, 1-methyl-1-propylpiperidinium 3-(methylthio)propanoate, 1-butyl-1-methylpiperidinium 3-(methylthio)propanoate, 1-allyl-1-methylpiperidinium 3-(methylthio)propanoate, 1-allyl-1-ethylpiperidinium 3-(methylthio)propanoate, 1-(2-methoxyethyl)-1-methylpiperidinium 3-(methylthio)propanoate, 1-(2-ethoxyethyl)-1-methylpiperidinium 3-(methylthio)propanoate, N,N-dimethylmorpholinium methoxyacetate, N-ethyl-N-methylmorpholinium methoxyacetate, N-methyl-N-propylmorpholinium methoxyacetate, N-butyl-N-methylmorpholinium methoxyacetate, N-allyl-N-methylmorpholinium methoxyacetate, N-allyl-N-ethylmorpholinium methoxyacetate, N-(2-methoxyethyl)-N-methylmorpholinium methoxyacetate, N-(2-ethoxyethyl)-N-methylmorpholinium methoxyacetate, N,N-dimethylmorpholinium 3-(2-methoxyethoxy)propanoate, N-ethyl-N-methylmorpholinium 3-(2-methoxyethoxy)propanoate, N-methyl-N-propylmorpholinium 3-(2-methoxyethoxy)propanoate, N-butyl-N-methylmorpholinium 3-(2-methoxyethoxy)propanoate, N-allyl-N-methylmorpholinium 3-(2-methoxyethoxy)propanoate, N-allyl-N-ethylmorpholinium 3-(2-methoxyethoxy)propanoate, N-(2-methoxyethyl)-N-methylmorpholinium 3(2-methoxyethoxy)propanoate, N-(2-ethoxyethyl)-N-methylmorpholinium 3-(2-methoxyethoxy)propanoate, N,N-dimethylmorpholinium 3-(2-ethoxyethoxy)propanoate, N-ethyl-N-methylmorpholinium 3-(2-ethoxyethoxy)propanoate, N-methyl-N-propylmorpholinium 3-(2-ethoxyethoxy)propanoate, N-butyl-N-methylmorpholinium 3-(2-ethoxyethoxy)propanoate, N-allyl-N-methylmorpholinium 3-(2-ethoxyethoxy)propanoate, N-allyl-N-ethylmorpholinium 3-(2-ethoxyethoxy)propanoate, N-(2-methoxyethyl)-N-methylmorpholinium 3-(2-ethoxyethoxy)propanoate, N-(2-ethoxyethyl)-N-methylmorpholinium 3-(2-ethoxyethoxy)propanoate, N,N-dimethylmorpholinium 3-[2-(2-methoxyethoxy)ethoxy]propanoate, N-ethyl-N-methylmorpholinium 3-[2-(2-methoxyethoxy)ethoxy]propanoate, N-methyl-N-propylmorpholinium 3-[2-(2-methoxyethoxy)ethoxy]propanoate, N-butyl-N-methylmorpholinium 3-[2-(2-methoxyethoxy)ethoxy]propanoate, N-allyl-N-methylmorpholinium 3-[2-(2-methoxyethoxy)ethoxy]propanoate, N-allyl-N-ethylmorpholinium 3-[2-(2-methoxyethoxy)ethoxy]propanoate, N-(2-methoxyethyl)-N-methylmorpholinium 3-[2-(2-methoxyethoxy)ethoxy]propanoate, N-(2-ethoxyethyl)-N-methylmorpholinium 3-[2-(2-methoxyethoxy)ethoxy]propanoate, N,N-dimethylmorpholinium 4,7,10,13-tetraoxatetradecanoate, N-ethyl-N-methylmorpholinium 4,7,10,13-tetraoxatetradecanoate, N-methyl-N-propylmorpholinium 4,7,10,13-tetraoxatetradecanoate, N-butyl-N-methylmorpholinium 4,7,10,13-tetraoxatetradecanoate, N-allyl-N-methylmorpholinium 4,7,10,13-tetraoxatetradecanoate, N-allyl-N-ethylmorpholinium 4,7,10,13-tetraoxatetradecanoate, N-(2-methoxyethyl)-N-methylmorpholinium 4,7,10,13-tetraoxatetradecanoate, N-(2-ethoxyethyl)-N-methylmorpholinium 4,7,10,13-tetraoxatetradecanoate, N,N-dimethylmorpholinium 3-(methylthio)propanoate, N-ethyl-N-methylmorpholinium 3-(methylthio)propanoate, N-methyl-N-propylmorpholinium 3-(methylthio)propanoate N-butyl-N-methylmorpholinium 3-(methylthio)propanoate, N-allyl-N-methylmorpholinium 3-(methylthio)propanoate, N-allyl-N-ethylmorpholinium 3-(methylthio)propanoate, N-(2-methoxyethyl)-N-methylmorpholinium 3-(methylthio)propanoate, N-(2-ethoxyethyl)-N-methylmorpholinium 3-(methylthio)propanoate, 1-methylpyridinium methoxyacetate, 1-ethylpyridinium methoxyacetate, 1-propylpyridinium methoxyacetate, 1-butylpyridinium methoxyacetate, 1-allylpyridinium methoxyacetate, 1-(2-methoxyethyl)pyridinium methoxyacetate, 1-(2-ethoxyethyl)pyridinium methoxyacetate, 1-methylpyridinium 3-(2-methoxyethoxy)propanoate, 1-ethylpyridinium 3-(2-methoxyethoxy)propanoate, 1-propylpyridinium 3-(2-methoxyethoxy)propanoate, 1-butylpyridinium 3-(2-methoxyethoxy)propanoate, 1-allylpyridinium 3-(2-methoxyethoxy)propanoate, 1-(2-methoxyethyl)pyridinium 3-(2-methoxyethoxy)propanoate, 1-(2-ethoxyethyl)pyridinium 3-(2-methoxyethoxy)propanoate, 1-methylpyridinium 3-(2-ethoxyethoxy)propanoate, 1-ethylpyridinium 3-(2-ethoxyethoxy)propanoate, 1-propylpyridinium 3-(2-ethoxyethoxy)propanoate, 1-butylpyridinium 3-(2-ethoxyethoxy)propanoate, 1-allylpyridinium 3-(2-ethoxyethoxy)propanoate, 1-(2-methoxyethyl)pyridinium 3-(2-ethoxyethoxy)propanoate, 1-(2-ethoxyethyl)pyridinium 3-(2-ethoxyethoxy)propanoate, 1-methylpyridinium 3-[2-(2-methoxyethoxy)ethoxy]propanoate, 1-ethylpyridinium 3-[2-(2-methoxyethoxy)ethoxy]propanoate, 1-propylpyridinium 3-[2-(2-methoxyethoxy)ethoxy]propanoate, 1-butylpyridinium 3-[2-(2-methoxyethoxy)ethoxy]propanoate, 1-allylpyridinium 3-[2-(2-methoxyethoxy)ethoxy]propanoate, 1-(2-methoxyethyl)pyridinium 3-[2-(2-methoxyethoxy)ethoxy]propanoate, 1-(2-ethoxyethyl)pyridinium 3-[2-(2-methoxyethoxy)ethoxy]propanoate, 1-methylpyridinium 4,7,10,13-tetraoxatetradecanoate, 1-ethylpyridinium 4,7,10,13-tetraoxatetradecanoate, 1-propylpyridinium 4,7,10,13-tetraoxatetradecanoate, 1-butylpyridinium 4,7,10,13-tetraoxatetradecanoate, 1-(2-methoxy ethyl)pyridinium 4,7,10,13-tetraoxatetradecanoate, 1-(2-ethoxyethyl)pyridinium 4,7,10,13-tetraoxatetradecanoate, 1-methylpyridinium 3-(methylthio)propanoate, 1-ethylpyridinium 3-(methylthio)propanoate, 1-propylpyridinium 3-(methylthio)propanoate, 1-butylpyridinium 3-(methylthio)propanoate, 1-allylpyridinium 3-(methylthio)propanoate, 1-(2-methoxyethyl)pyridinium 3-(methylthio)propanoate, 1-(2-ethoxyethyl)pyridinium 3-(methylthio)propanoate, 1,3-dimethylimidazolium methoxyacetate, 1-ethyl-3-methylimidazolium methoxyacetate, 1-methyl-3-propylimidazolium methoxyacetate, 1-butyl-3-methylimidazolium methoxyacetate, 1-allyl-3-methylimidazolium methoxyacetate, 1-allyl-3-ethylimidazolium methoxyacetate, 1-(2-methoxy ethyl)-3-methylimidazolium methoxyacetate, 1-(2-ethoxy ethyl)-3-methylimidazolium methoxyacetate, 1-ethyl-3-(2-methoxyethyl)imidazolium methoxyacetate, 1-ethyl-3-(2-ethoxyethyl)imidazolium methoxyacetate, 1,3-dimethylimidazolium 3-(2-methoxyethoxy)propanoate, 1-ethyl-3-methylimidazolium 3-(2-methoxyethoxy)propanoate, 1-methyl-3-propylimidazolium 3-(2-methoxyethoxy)propanoate, 1-butyl-3-methylimidazolium 3-(2-methoxyethoxy)propanoate, 1-allyl-3-methylimidazolium 3-(2-methoxyethoxy)propanoate, 1-allyl-3-ethylimidazolium 3-(2-methoxyethoxy)propanoate, 1-(2-methoxyethyl)-3-methylimidazolium 3-(2-methoxyethoxy)propanoate, 1-(2-ethoxyethyl)-3-methylimidazolium 3-(2-methoxyethoxy)propanoate, 1-ethyl-3-(2-methoxyethyl)imidazolium 3-(2-methoxyethoxy)propanoate, 1-ethyl-3-(2-ethoxyethyl)imidazolium 3-(2-methoxyethoxy)propanoate, 1,3-dimethylimidazolium 3-(2-ethoxyethoxy)propanoate, 1-ethyl-3-methylimidazolium 3-(2-ethoxyethoxy)propanoate, 1-methyl-3-propylimidazolium 3-(2-ethoxyethoxy)propanoate, 1-butyl-3-methylimidazolium 3-(2-ethoxyethoxy)propanoate, 1-allyl-3-methylimidazolium 3-(2-ethoxyethoxy)propanoate, 1-allyl-3-ethylimidazolium 3-(2-ethoxyethoxy)propanoate, 1-(2-methoxyethyl)-3-methylimidazolium 3-(2-ethoxyethoxy)propanoate, 1-(2-ethoxyethyl)-3-methylimidazolium 3-(2-ethoxyethoxy)propanoate, 1-ethyl-3-(2-methoxyethyl)imidazolium 3-(2-ethoxyethoxy)propanoate, 1-ethyl-3-(2-ethoxyethyl)imidazolium 3-(2-ethoxyethoxy)propanoate, 1,3-dimethylimidazolium 3-[2-(2-methoxyethoxy)ethoxy]propanoate, 1-ethyl-3-methylimidazolium 3-[2-(2-methoxyethoxy) ethoxy]propanoate, 1-methyl-3-propylimidazolium 3-[2-(2-methoxyethoxy)ethoxy]propanoate, 1-butyl-3-methylimidazolium 3-[2-(2-methoxyethoxy)

ethoxy]propanoate, 1-allyl-3-methylimidazolium 3-[2-(2-methoxyethoxy)ethoxy]propanoate, 1-allyl-3-ethylimidazolium 3-[2-(2-methoxyethoxy)ethoxy]propanoate, 1-(2-methoxyethyl)-3-methylimidazolium 3-[2-(2-methoxyethoxy)ethoxy]propanoate, 1-(2-ethoxyethyl)-3-methylimidazolium 3-[2-(2-methoxyethoxy)ethoxy]propanoate, 1-ethyl-3-(2-methoxyethyl)imidazolium 3-[2-(2-methoxyethoxy)ethoxy]propanoate, 1-ethyl-3-(2-ethoxyethyl)imidazolium 3-[2-(2-methoxyethoxy)ethoxy]propanoate, 1,3-dimethylimidazolium 4,7,10,13-tetraoxatetradecanoate, 1-ethyl-3-methylimidazolium 4,7,10,13-tetraoxatetradecanoate, 1-methyl-3-propylimidazolium 4,7,10,13-tetraoxatetradecanoate, 1-butyl-3-methylimidazolium 4,7,10,13-tetraoxatetradecanoate, 1-allyl-3-methylimidazolium 4,7,10,13-tetraoxatetradecanoate, 1-allyl-3-ethylimidazolium 4,7,10,13-tetraoxatetradecanoate, 1-(2-methoxyethyl)-3-methylimidazolium 4,7,10,13-tetraoxatetradecanoate, 1-(2-ethoxyethyl)-3-methylimidazolium 4,7,10,13-tetraoxatetradecanoate, 1-ethyl-3-(2-methoxyethyl)imidazolium 4,7,10,13-tetraoxatetradecanoate, 1-ethyl-3-(2-ethoxyethyl)imidazolium 4,7,10,13-tetraoxatetradecanoate, 1,3-dimethylimidazolium 3-(methylthio)propanoate, 1-ethyl-3-methylimidazolium 3-(methylthio)propanoate 1-methyl-3-propylimidazolium 3-(methylthio)propanoate, 1-butyl-3-methylimidazolium 3-(methylthio)propanoate, 1-allyl-3-methylimidazolium 3-(methylthio)propanoate, 1-allyl-3-ethylimidazolium 3-(methylthio)propanoate, 1-(2-methoxyethyl)-3-methylimidazolium 3-(methylthio)propanoate, 1-(2-ethoxyethyl)-3-methylimidazolium 3-(methylthio)propanoate, 1-ethyl-3-(2-methoxyethyl)imidazolium 3-(methylthio)propanoate, and 1-ethyl-3-(2-ethoxyethyl)imidazolium 3-(methylthio)propanoate, preferred examples thereof include N,N,N-trimethyl-N-propylammonium methoxyacetate, N,N,N-trimethyl-N-propylammonium 3-(2-methoxyethoxy)propanoate, N,N,N-trimethyl-N-propylammonium 3-(2-ethoxyethoxy)propanoate, N,N,N-trimethyl-N-propylammonium 3-(methylthio)propanoate, N,N,N-trimethyl-N-propylammonium 3-[2-(2-methoxyethoxy)ethoxy]propanoate, N,N,N-trimethyl-N-propylammonium 4,7,10,13-tetraoxatetradecanoate, N-butyl-N,N-diethyl-N-methylammonium methoxyacetate, N-butyl-N,N-diethyl-N-methylammonium 3-(2-methoxyethoxy)propanoate, N-butyl-N,N-diethyl-N-methylammonium 3-(2-ethoxyethoxy)propanoate, N-butyl-N,N-diethyl-N-methylammonium 3-(methylthio)propanoate, N-butyl-N,N-diethyl-N-methylammonium 3-[2-(2-methoxyethoxy)ethoxy]propanoate, N-butyl-N,N-diethyl-N-methylammonium 4,7,10,13-tetraoxatetradecanoate, N,N-diethyl-N-(2-methoxyethyl)-N-methylammonium methoxyacetate, N,N-diethyl-N-(2-methoxyethyl)-N-methylammonium 3-(2-methoxyethoxy)propanoate, N,N-diethyl-N-(2-methoxyethyl)-N-methylammonium 3-(2-ethoxyethoxy)propanoate, N,N-diethyl-N-(2-methoxyethyl)-N-methylammonium 3-[2-(2-methoxyethoxy)ethoxy]propanoate, N,N-diethyl-N-(2-methoxyethyl)-N-methylammonium 4,7,10,13-tetraoxatetradecanoate, N-ethyl-N-[2-(2-methoxyethoxy)ethyl]-N,N-dimethylammonium methoxyacetate, N-ethyl-N-[2-(2-methoxyethoxy)ethyl]-N,N-dimethylammonium 3-(2-methoxyethoxy)propanoate, N-ethyl-N-[2-(2-methoxyethoxy)ethyl]-N,N-dimethylammonium 3-(2-ethoxyethoxy)propanoate, N-ethyl-N-[2-(2-methoxyethoxy)ethyl]-N,N-dimethylammonium 3-(methylthio)propanoate, N-ethyl-N-[2-(2-methoxyethoxy)ethyl]-N,N-dimethylammonium 3-[2-(2-methoxyethoxy)ethoxy]propanoate, N-ethyl-N-[2-(2-methoxyethoxy)ethyl]-N,N-dimethylammonium 4,7,10,13-tetraoxatetradecanoate, N-allyl-N-methylmorpholinium methoxyacetate, N-allyl-N-methylmorpholinium 3-(2-methoxyethoxy)propanoate, N-allyl-N-methylmorpholinium 3-(2-ethoxyethoxy)propanoate, N-allyl-N-methylmorpholinium 3-(methylthio)propanoate, N-allyl-N-methylmorpholinium 3-[2-(2-methoxyethoxy)ethoxy]propanoate, N-allyl-N-methylmorpholinium 4,7,10,13-tetraoxatetradecanoate, 1-ethyl-3-methylimidazolium methoxyacetate, 1-ethyl-3-methylimidazolium 3-(2-methoxyethoxy)propanoate, 1-ethyl-3-methylimidazolium 3-(2-ethoxyethoxy)propanoate, 1-ethyl-3-methylimidazolium 3-(methylthio)propanoate, 1-ethyl-3-methylimidazolium 3-[2-(2-methoxyethoxy)ethoxy]propanoate, 1-ethyl-3-methylimidazolium 4,7,10,13-tetraoxatetradecanoate, 1-butyl-3-methylimidazolium methoxyacetate, 1-butyl-3-methylimidazolium 3-(2-methoxyethoxy)propanoate, 1-butyl-3-methylimidazolium 3-(2-ethoxyethoxy)propanoate, 1-butyl-3-methylimidazolium 3-(methylthio)propanoate, 1-butyl-3-methylimidazolium 3-[2-(2-methoxyethoxy)ethoxy]propanoate, and 1-butyl-3-methylimidazolium 4,7,10,13-tetraoxatetradecanoate, and particularly preferred examples thereof include N,N,N-trimethyl-N-propylammonium 3-(2-methoxyethoxy)propanoate, N-butyl-N,N-diethyl-N-methylammonium 3-(2-methoxyethoxy)propanoate, N-butyl-N,N-diethyl-N-methylammonium 3-(2-ethoxyethoxy)propanoate, N,N-diethyl-N-(2-methoxyethyl)-N-methylammonium methoxyacetate, N,N-diethyl-N-(2-methoxyethyl)-N-methylammonium 3-(2-methoxyethoxy)propanoate, N,N-diethyl-N-(2-methoxyethyl)-N-methylammonium 3-(2-ethoxyethoxy)propanoate, N,N-diethyl-N-(2-methoxyethyl)-N-methylammonium 3-(methylthio)propanoate, N-ethyl-N-[2-(2-methoxyethoxy)ethyl]-N,N-dimethylammonium methoxyacetate, N-ethyl-N-[2-(2-methoxyethoxy)ethyl]-N,N-dimethylammonium 3-(2-methoxyethoxy)propanoate, N-ethyl-N-[2-(2-methoxyethoxy)ethyl]-N,N-dimethylammonium 3-(methylthio)propanoate, N-allyl-N-methylmorpholinium methoxyacetate, N-allyl-N-methylmorpholinium 3-(2-methoxyethoxy)propanoate, N-ethyl-3-methylimidazolium 3-(2-methoxyethoxy)propanoate, N-ethyl-3-methylimidazolium 3-(2-ethoxyethoxy)propanoate, and N-butyl-3-methylimidazolium 3-(2-methoxyethoxy)propanoate, but the present invention is not limited to them.

The onium salt (1) can be produced by various methods. The representative method is explained on the basis of the following Reaction formula 1. In the reaction formula, $R^1$, $X^+$, $Y^+$, and a to c are as defined above and $A^-$ represents a halogen ion.

Reaction formula 1:

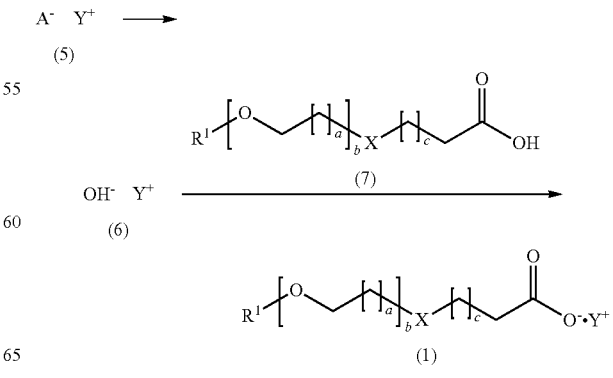

As for the onium salt (1), it is possible that onium halide represented by Formula (5) (hereinbelow, referred to as the halide salt (5)) is converted to onium hydroxide (hereinbelow, referred to as the hydroxide salt (6)) by ion exchange using an ion exchange resin, silver oxide, alkali metal salt, or the like (hereinbelow, referred to as the First reaction) and the obtained hydroxide salt (6) and the carboxylic acid represented by Formula (7) (hereinbelow, referred to as the carboxylic acid (7)) are subjected to ion exchange to provide the onium salt (1) (hereinbelow, referred to as the Second reaction).

First, explanations are given for the First reaction. Examples of the halide salt (5), which is used for the Reaction formula 1, include a compound in which halogen ions such as chloro ion, bromo ion, iodide ion, or the like represented by A$^-$ described above are combined with the cation Y$^+$.

As for the ion exchange resin used for the First reaction, a strong basic ion exchange resin that is commercially available as a resin for water treatment or a catalyst can be used, for example. The use amount of the ion exchange resin is, relative to 1 mol of the halide salt (5), generally 20 molar equivalents or less, preferably 1 to 10 molar equivalents, and particularly preferably 2 to 5 molar equivalents.

The amount of silver oxide used for the First reaction is, relative to 1 mol of the halide salt (5), generally 10 molar equivalents or less, preferably 0.5 to 2 molar equivalents, and particularly preferably 0.5 to 0.7 molar equivalent.

Examples of the alkali metal salt used for the First reaction include sodium hydroxide and potassium hydroxide. The use amount of the alkali metal salt is generally 3 molar equivalents or less relative to 1 mol of the halide salt (5).

The First reaction is generally carried out in a solvent. Examples of the solvent include acetone, alcohols such as methanol, ethanol, and 2-propanol, acetonitrile, ethyl acetate, and water. The use amount of the solvent is, although not particularly limited, generally 10 parts by mass or less, preferably 1 to 10 parts by mass, and particularly preferably 2 to 6 parts by mass relative to 1 parts by mass of the halide salt (5).

Reaction temperature of the First reaction is generally 10° C. or higher, preferably 10 to 60° C., and particularly preferably 10 to 30° C.

The reaction mixture obtained from the First reaction is generally used as it is for the Second reaction, or used for the Second reaction after insolubles are removed by filtration.

Examples of the hydroxide salt (6) which is obtained from the First reaction include a compound in which the aforementioned cation Y$^+$ is combined with OH$^-$.

Next, explanations are given for the Second reaction. Amount of the carboxylic acid (7), which is used for the Second reaction, is generally 0.8 molar equivalent or more, preferably 0.8 to 1.2 molar equivalents, and particularly preferably 0.9 to 1.1 molar equivalents relative to 1 mol of the hydroxide salt (6).

The Second reaction is generally carried out in a solvent. Examples of the solvent include ketones such as acetone and methyl ethyl ketone, alcohols such as methanol, ethanol, and 2-propanol, acetonitrile, ethyl acetate, tetrahydrofuran, dimethyl formamide and water. The use amount of the solvent is, although not particularly limited, generally 10 parts by mass or less, preferably 1 to 10 parts by mass, and particularly preferably 1 to 6 parts by mass relative to 1 part by mass of the hydroxide salt (6).

Reaction temperature of the Second reaction is generally 10° C. or higher, preferably 10 to 60° C., and particularly preferably 10 to 30° C.

By performing concentration of a reaction mixture obtained after completing the aforementioned reaction, the onium salt (1) can be obtained, for example. The obtained onium salt (1) can be further purified by a known method like recrystallization.

By mixing two or more kinds, the onium salt (1) can be also used as mixed onium salt (hereinbelow, referred to as the mixed onium salt (8)).

In the present invention, the cellulose-containing liquid composition contains cellulose and the onium salt (1) or the mixed onium salt (8), in which the cellulose is dissolved in the onium salt (1) or the mixed onium salt (8).

The cellulose-containing liquid composition may further contain an organic solvent. Examples of the organic solvent to be contained in the cellulose-containing liquid composition include N,N-dimethylacetamide, dimethyl sulfoxide, N,N-dimethylformamide, and organic solvents in which at least two of those organic solvents are mixed. In that case, the cellulose-containing liquid composition is obtained by dissolving cellulose in a medium containing the onium salt (1) or the mixed onium salt (8) and those organic solvents.

Ratio of the onium salt (1) or the mixed onium salt (8) and the organic solvent in the medium of the cellulose-containing liquid composition [weight of the onium salt (1) or weight of the mixed onium salt (8)/(weight of the onium salt (1) or weight of the mixed onium salt (8)+weight of organic solvent)×100] is generally 5 to 80% by weight, preferably 9 to 70% by weight, and more preferably 10 to 70% by weight Cellulose described in the present invention indicates a polymer in which glucose is polymerized by β-1,4-glucoside bond, and derivatives thereof. The polymerization degree of glucose in cellulose is, although not particularly limited, preferably 200 or more. Examples of the derivatives include derivatives by carboxymethylation, aldehydation, or esterification. Cellulose may also contain cellooligosaccharide or cellobiose, which are partial hydrolyzates of cellulose. Further, cellulose can be β glucoside as glycoside, lignocelluose as a complex with lignin and/or hemicelluloses, or a complex with pectin. Cellulose can be crystalline cellulose or non-crystalline cellulose. It is preferably crystalline cellulose. Further, cellulose can be natural product-derived or artificially synthesized one. Origin of cellulose is not particularly limited. It can be derived from a plant, a fungus, or a microbe.

Materials containing cellulose are also included in the aforementioned cellulose. Examples of the material containing cellulose include a natural fiber product such as cotton and linen, a recycled fiber product such as rayon, cupra, and acetate, various straws such as rice straw, burgess, agricultural waste products such as wood chips, used paper, and biomass containing various waste product such as construction waste.

Next, explanations are given for the method for recovering cellulose of the present invention. First, by dissolving cellulose in a medium containing the onium salt (1) or the mixed onium salt (8), or a medium containing the onium salt (1) or the mixed onium salt (8) and the organic solvent described above, a cellulose-containing liquid composition is obtained. By adding a poor solvent to the obtained cellulose-containing liquid composition, cellulose is precipitated in a mixed solution. The precipitated cellulose is separated from the mixed solution by filtration or the like. The separated cellulose can be recovered as cellulose by drying. Further, by evaporating the poor solvent and organic solvent by an operation such as concentration from the mixed solution from which cellulose has been separated, the onium salt (1) or the mixed onium salt (8) can be recovered.

Temperature for dissolving cellulose in the medium is not particularly limited if the medium shows a liquid phase within the temperature range. From the viewpoint of operation, it is preferably 60° C. to 120° C.

Examples of the poor solvent which is used for recovering cellulose include methanol, ethanol, acetone, and a mixed solvent thereof.

Method for adding a poor solvent is not particularly limited, but a method of adding dropwise a poor solvent to the cellulose-containing liquid composition and the like is employed.

Next, the present invention is described specifically based on Examples, but the present invention is not at all limited to them. In Examples, $^1$H-NMR was measured at 400 MHz by using AV400 manufactured by Bruker Corporation. In Table 2, the solubility means % by weight of cellulose dissolved in 1.00 g of onium salt [(weight of cellulose dissolved in onium salt/weight of onium salt)×100)]. In Table 3, the solubility means % by weight of cellulose dissolved in 1.00 g of medium in which an onium salt and an organic solvent are mixed or 1.00 g of an organic solvent [(weight of cellulose dissolved in medium in which an onium salt and an organic solvent are mixed or in organic solvent/weight of medium in which an onium salt and an organic solvent are mixed or an organic solvent)×100)]. N,N-diethyl-N-(2-methoxyethyl)-N-methylammonium is abbreviated as [$N_{221ME}$], N-ethyl-N-[2-(2-methoxyethoxy) ethyl]-N,N-dimethylammonium is abbreviated as [$N_{211MEE}$], N-allyl-N-methylmorpholine is abbreviated as [$N_{AMM}$], N-butyl-N,N-diethyl-N-methylammonium is abbreviated as [$N_{1224}$], N,N,N-trimethyl-N-propylammonium is abbreviated as [$N_{1113}$], 1-ethyl-3-methylimidazolium is abbreviated as [$C_2$mim], 1-butyl-3-methylimidazolium is abbreviated as [$C_4$mim], 3-(2-methoxyethoxy) propanoic acid is abbreviated as [MEEPA], 3-(2-ethoxyethoxy)propanoic acid is abbreviated as [EEEPA], methoxyacetic acid is abbreviated as [MEAA], 3-(methylthio)propanoic acid is abbreviated as [MSPA], 3-[2-(2-methoxyethoxy)ethoxy]propanoic acid is abbreviated as [MEEEPA], 4,7,10,13-tetraoxatetradecanoic acid is abbreviated as [TOTA], chloride is abbreviated as [Cl], bromide is abbreviated as [Br], acetate is abbreviated as [Ac], and 2-aminopropanoic acid is abbreviated as [Ala].

PREPARATION EXAMPLE 1

Synthesis of 3-(2-methoxyethoxy)propanoic acid

To a 3 L four neck flask purged with nitrogen, 16333 g (21.46 mol) of 2-methoxyethanol was added. After cooling to 0° C., 413 g (1.80 mol) of sodium metal was added thereto. After confirming no gas generation from the resulting reaction solution, 164.2 g (1.64 mol) of ethyl acrylate was slowly added dropwise thereto. Once the dropwise addition is completed, the reaction solution was heated from 0° C. to room temperature and then stirred for 24 hours at room temperature. The resulting reaction solution was dried under reduced pressure and added with 164.0 g of ion exchange water. After adjusting the reaction solution to pH=4 by using 10% aqueous solution of sulfuric acid, extraction was performed by using 1408.4 g of ethyl acetate. The obtained organic layer was dried under reduced pressure to obtain 57.6 g of 2-methoxyethoxypropanoic acid (yield: 24%).

$^1$H-NMR analysis data of the obtained 3-(2-methoxyethoxy)propanoic acid is given below.
$^1$H-NMR(CDCl$_3$) δ(ppm)=3.78(t,2H), 3.64(t,2H), 3.56(t, 2H), 3.39(s,3H) 2.66(t,2H)

PREPARATION EXAMPLE 2

Synthesis of 3-(2-ethoxyethoxy)propanoic acid 36.92 g of 3-(2-ethoxyethoxy)propanoic acid (yield: 74%) was obtained in the same manner as Preparation Example 1 except that 2-methoxyethanol of Preparation Example 1 was replaced with 2-ethoxyethanol.

$^1$H-NMR analysis data of the obtained 3-(2-ethoxyethoxy)propanoic acid is given below.
$^1$H-NMR(CDCl3) δ(ppm)=3.84(t,2H), 3.65(t,2H), 3.61(t, 2H), 3.49(q,2H) 2.68(t,2H), 1.24(t,3H)

PREPARATION EXAMPLE 3

Synthesis of 3-(methylthio)propanoic acid

To a 200 mL four neck flask, 6.67 g (49.70 mmol) of methyl 3-(methylthio)propanoic acid, 13.58 g of ion exchange, and 2.04 g (51.03 mmol) of sodium hydroxide was added and stirred at room temperature for 16 hours. To the reaction solution, 54.22 g of 1 mol/L hydrochloric acid were added for neutralization followed by addition of 7.61 g of ethyl acetate for extraction. The obtained organic layer was washed with 4.42 g of ion exchange water and then dried under reduced pressure to obtain 4.45 g of 3-(methylthio)propanoic acid (yield: 75%).

$^1$H-NMR analysis data of the obtained 3-(methylthio) propanoic acid is given below.
$^1$H-NMR(DMSO-d$_6$) δ(ppm)=2.67(t,2H), 2.51(t,2H), 2.07(s,3H)

PREPARATION EXAMPLE 4

Synthesis of 3-[2-(2-methoxyethoxy)ethoxy]propanoic acid

To a 500 mL four neck flask purged with argon, 110 mL (0.93 mol) of 2-(2-methoxyethoxy)ethanol and 50 mL of dehydrated THF were added. After cooling to 0° C., 1.4 g (0.06 mol) of sodium metal was added thereto. After confirming no gas generation from the resulting reaction solution, a solution in which 44 mL (0.31 mol) of tertiary butyl acrylate is diluted in 50 mL of THF was slowly added dropwise thereto. Once the dropwise addition is completed, the reaction solution was heated from 0° C. to room temperature and then stirred for 24 hours at room temperature. The resulting reaction solution was dried under reduced pressure for removing THF by distillation. Then, 100 mL (0.3 mol) of 3 mol/L aqueous solution of sodium hydroxide was added and stirred for 5 hours. After adjustment to have pH=2 by adding 10% aqueous solution of sulfuric acid to the obtained reaction solution, extraction was performed three times by using methylene chloride. The obtained organic layer was dried over anhydrous magnesium sulfate and dried under reduced pressure. The obtained crude 3-[2-(2-methoxyethoxy)ethoxy]propanoic acid was distilled twice under reduced pressure at 140° C., 0.1 kPa to obtain 14 g of 3-[2-(2-methoxymethyl)ethoxy]propanoic acid (yield: 24%).

$^1$H-NMR analysis data of the obtained 3-[2-(2-methoxyethoxy)ethoxy]propanoic acid is given below.

$^1$H-NMR(DMSO-d$_6$) δ(ppm)=2.67(q,2H), 2.51(q,2H), 2.07(s,3H)

PREPARATION EXAMPLE 5

Synthesis of 4,7,10,13-tetraoxatetradecanoic acid 39 g of 4,7,10,13-tetraoxatetradecanoic acid (yield: 54%) was obtained in the same manner as Preparation Example 4 except that 2-(2-methoxyethoxy)ethanol of Preparation Example 4 was replaced with 2-[2-(2-ethoxyethoxy)ethoxy]ethanol.

$^1$H-NMR analysis data of the obtained 4,7,10,13-tetraoxatetradecanoic acid is given below.

$^1$H-NMR(CDCl3) δ(ppm)=3.80(t,2H), 3.71-3.65(m, 10H), 3.60(t,2H), 3.42(s,3H), 2.65(t,2H)

EXAMPLE 1-1

To a 5 L four neck flask, 632.52 g (3.49 mol) of N,N-diethyl-N-(2-methoxyethyl)-N-methylammonium chloride and 3168.18 g of methanol were added and stirred at room temperature. 445.02 g (1.92 mol) of silver (I) oxide was added thereto over 1 hour and stirred for 21 hours at room temperature. The reaction solution was filtered and the residues were washed with 173.55 g of methanol to obtain methanol solution of N,N-diethyl-N-(2-methoxyethyl)-N-methylammonium hydroxide as a filtrate. 4.81 g (5.72 mmol) was drawn from the obtained methanol solution of N,N-diethyl-N-(2-methoxyethyl)-N-methylammonium hydroxide, and 0.89 g (6.01 mmol) of 3-(2-methoxyethoxy)propanoic acid, which has been obtained from Preparation Example 1, was added thereto at room temperature followed by stirring for 12 hours at room temperature. The reaction solution was concentrated to obtain 1.69 g of N,N-diethyl-N-(2-methoxyethyl)-N-methylammonium 3-(2-methoxyethoxy)propanoate (hereinbelow, abbreviated as [$N_{221ME}$][MEEPA]) (total yield: 100%).

$^1$H-NMR analysis data of the obtained [$N_{221ME}$][MEEPA] is given below.

$^1$H-NMR(CDCl$_3$) δ(ppm)=3.82-3.70(m,4H), 3.58-3.41(m,9H), 3.37-3.34(m,7H), 3.19(s,3H), 2.51(t,2H), 1.66(t, 6H)

EXAMPLES 1-2, 1-3, 2-1, AND 2-2

The onium salt (1) was obtained in the same manner as Example 1-1 except that N,N-diethyl-N-(2-methoxyethyl)-N-methylammonium chloride of Example 1-1 was replaced with the halide salt (5) shown in Table 1.

$^1$H-NMR analysis data of the [$N_{1224}$][MEEPA] is given below.

$^1$H-NMR(CDCl$_3$) δ(ppm)=71(t,2H), 3.57(dq,2H), 3.53(dq,2H), 3.44(q,4H), 3.41-3.20(m,2H), 3.34(s,3H), 3.09(s, 3H), 2.42(q,2H), 1.69-1.61(m,2H), 1.46-1.32(m,2H), 1.35(t, 6H), 0.99(t,3H)

$^1$H-NMR analysis data of the [$N_{1113}$][MEEPA] is given below.

$^1$H-NMR(CDCl$_3$) δ(ppm)=3.73(t,2H), 3.57(t,2H), 3.51(t, 2H), 3.38(t,3H), 3.25(s,3H), 2.27(s,9H), 2.42(t,2H), 1.83-1.73(m,2H), 1.02(t,3H)

$^1$H-NMR analysis data of the [$N_{21MEE}$][MEEPA] is given below.

$^1$H-NMR(DMSO-d$_6$) δ(ppm)=3.01(br,2H), 2.96-2.66(m, 14H), 2.53(s,3H), 2.51(s,3H), 2.32(s,6H), 1.33(t,2H), 0.50(t,3H)

$^1$H-NMR analysis data of the [$N_{AMM}$][MEEPA] is given below.

$^1$H-NMR(DMSO-d$_6$) δ(ppm)=6.06 (dt,1H), 5.67(dd,2H), 4.13 (d,4H), 3.94 (t,4H), 3.48-3.35 (m,8H), 3.24(s,3H), 3.17(s,3H), 2.01(t,2H)

EXAMPLE 1-4

170 mL (102 mmol) of ion exchange resin (DOWEX (registered trademark), manufactured by The Dow Chemical Company) was admixed with ion exchanged water and filled in a column. Then, a solution in which 5.01 g (34.17 mmol) of 1-ethyl-3-methylimidazolium chloride was dissolved in 30.48 g of ion exchanged water was allowed to flow through it two times. Further, 19.99 g of ion exchanged water was divided to two portions and allowed to flow through the ion exchange resin to obtain 79.64 g of a reaction solution. From the obtained reaction solution, 13.66 g (5.85 mmol) was drawn and then added with 0.86 g (5.84 mmol) of 3-(2-methoxyethoxy)propanoic acid, which has been obtained in Preparation Example 1, followed by stirring for 24 hours at room temperature. The resulting reaction solution was concentrated and dried to obtain 1.38 g of 1-ethyl-3-methylimidazolium 3-(2-methoxyethoxy)propanoate (hereinbelow, abbreviated as [$C_2$mim][MEEPA]) (yield: 91%).

$^1$H-NMR analysis data of the obtained [$C_2$mim][MEEPA] is given below.

$^1$H-NMR(CDCl$_3$) δ(ppm)=10.79(s,1H), 7.49(s,1H), 7.48(s,1H), 4.33(q,2H), 4.03(s,3H), 3.79(t,2H), 3.60(t,2H), 3.52(t,2H), 3.33(s,3H), 2.52(t,2H), 1.55(t,3H)

EXAMPLE 1-5

The onium salt (1) was obtained in the same manner as Example 1-4 except that 1-ethyl-3-methylimidazolium chloride of Example 1-4 was replaced with the halide salt (5) shown in Table 1.

$^1$H-NMR analysis data of the [$C_4$mim][MEEPA] is given below.

$^1$H-NMR(CDCl$_3$) δ(ppm)=7.62(s,1H), 7.47(s,1H), 7.16(s, 1H), 4.29(t,2H), 4.05(s,3H), 3.82(t,2H), 3.72(t,2H), 3.61(t, 2H), 3.35 (s,3H), 2.55(t,2H), 1.89-1.82(m,211), 1.40-1.32(m,2H), 0.96(t,3H)

EXAMPLE 1-6

To a 5 L four neck flask, 632.52 g (3.49 mol) of N,N-diethyl-N-(2-methoxyethyl)-N-methylammonium chloride and 3168.18 g of methanol were added and stirred at room temperature. 445.02 g (1.92 mol) of silver (I) oxide was added thereto over 1 hour and stirred for 21 hours at room temperature. The reaction solution was filtered and the residue was washed with 173.55 g of methanol to obtain methanol solution of N,N-diethyl-N-(2-methoxyethyl)-N-methylammonium hydroxide as a filtrate. 5.78 g (6.88 mmol) was drawn from the obtained methanol solution of N,N-diethyl-N-(2-methoxyethyl)-N-methylammonium hydroxide, and 1.14 g (6.08 mmol) of 3-(2-ethoxyethoxy)propanoic acid, which has been obtained from Preparation Example 2, was added thereto followed by stirring for 12 hours at room temperature. The reaction solution was concentrated and dried to obtain 1.99 g of N,N-diethyl-N-(2-methoxyethyl)-N-methylammonium 3-(2-ethoxyethoxy)propanoate (hereinbelow, abbreviated as [$N_{221ME}$][EEEPA]) (total yield: 95%).

$^1$H-NMR analysis data of the obtained [$N_{221ME}$][EEEPA] is given below.

$^1$H-NMR(CDCl$_3$) δ(ppm)=3.97-3.84(m,4H), 3.77(t,2H), 3.56-3.42(m,10H), 3.36(s,3H), 3.23 (s,3H), 2.46(t,2H), 1.36 (t,6H), 1.17(t,3H)

EXAMPLE 1-7

The onium salt (1) was obtained in the same manner as Example 1-6 except that N,N-diethyl-N-(2-methoxyethyl)-N-methylammonium chloride of Example 1-6 was replaced with the halide salt (5) shown in Table 1.

$^1$H-NMR analysis data of the [N$_{1224}$] [EEEPA] is given below.

$^1$H-NMR(CDCl$_3$) δ(ppm)=3.72(t,2H), 3.57-3.56(m,4H), 3.55-3.46(m,2H), 3.53(q,4H), 3.38(q,2H), 3.01(s,3H), 2.45 (t,2H), 1.69-1.61(m,2H), 1.42(m,2H), 1.33(q,6H), 1.21(t, 3H), 0.98(t,3H)

EXAMPLE 1-8

170 mL (102 mmol) of ion exchange resin (DOWEX (registered trademark), manufactured by The Dow Chemical Company) was admixed with ion exchanged water and filled in a column. Then, a solution in which 5.01 g (34.17 mmol) of 1-ethyl-3-methylimidazolium chloride is dissolved in 30.48 g of ion exchanged water was allowed to flow through it two times. Further, 19.99 g of ion exchanged water was divided to two portions and allowed to flow through the ion exchange resin to give 79.64 g of a reaction solution. From the resulting reaction solution, 50.04 g was drawn and added with 4.43 g (23.62 mmol) of 3-(2-ethoxyethoxy)propanoic acid, which has been obtained in Preparation Example 2, followed by stirring for 24 hours at room temperature. The resulting reaction solution was concentrated and dried to obtain 6.20 g of 1-ethyl-3-methylimidazolium 3-(2-ethoxyethoxy)propanoate (hereinbelow, abbreviated as [C$_2$mim] [EEEPA]) (yield: 100%).

$^1$H-NMR analysis data of the obtained [C$_2$mim] [EEEPA] is given below.

$^1$H-NMR(CDCl$_3$) δ(ppm)=10.45(s,1H), 10.09(br,2H), 4.32(q,2H), 4.01(s,3H), 3.60(t,2H), 3.55-3.51(m,4H), 3.49 (q,3H), 2.52(q,2H), 1.56-1.51(m,2H), 1.15(t,3H)

EXAMPLE 2-3

To a 5 L four neck flask, 632.52 g (3.49 mol) of N,N-diethyl-N-(2-methoxyethyl)-N-methylammonium chloride and 3168.18 g of methanol were added and stirred at room temperature. 445.02 g (1.92 mol) of silver (I) oxide was added thereto over 1 hour and stirred for 21 hours at room temperature. The reaction solution was filtered and the residue was washed with 173.55 g of methanol to obtain methanol solution of N,N-diethyl-N-(2-methoxyethyl)-N-methylammonium hydroxide as a filtrate. 17.86 g (21.29 mmol) was drawn from the obtained methanol solution of N,N-diethyl-N-(2-methoxyethyl)-N-methylammonium hydroxide, and 1.92 g (21.31 mmol) of methoxyacetic acid was added thereto at room temperature followed by stirring for 12 hours at room temperature. The reaction solution was concentrated and dried to obtain 5.03 g of N,N-diethyl-N-(2-methoxyethyl)-N-methylammonium methoxyacetate (hereinbelow, abbreviated as [N$_{221ME}$] [MEAA]) (total yield: 100%).

$^1$H-NMR analysis data of the obtained [N$_{221ME}$] [MEAA] is given below.

$^1$H-NMR(DMSO-d$_6$) δ(ppm)=3.72(br,2H), 3.58(t,2H), 3.51(s,2H), 3.39(q,4H), 3.28(s,3H), 3.19(s,3H), 3.07(s,31-1), 1.19(t,6H)

EXAMPLE 2-4

The onium salt (1) was obtained in the same manner as Example 2-3 except that N,N-diethyl-N-(2-methoxyethyl)-N-methylammonium chloride of Example 2-3 was replaced with the halide salt (5) shown in Table 1.

$^1$H-NMR analysis data of the [N$_{211MEE}$] [MEAA] is given below.

$^1$H-NMR(DMSO-d$_6$) δ(ppm)=3.13(br,2H), 3.01-2.89(m, 2H), 2.88(t,2H), 2.79-2.77(m,4H), 2.73(q,2H), 2.57(s,3H), 2.50(s,3H), 2.36(s,6H), 1.19(t,3H)

EXAMPLE 2-5

To a 500 mL four neck flask, 30.00 g (29.66 mmol) of N-methylmorpholine and 60.00 g of acetonitrile were added and stirred at room temperature. 23.80 g (31.14 mmol) of allyl chloride was added dropwise thereto and stirred for 24 hours at room temperature. The resulting reaction solution was filtered and the residue were washed with acetonitrile. The obtained filtrate was concentrated and dried to obtain 35.23 g (yield: 67%) of N-allyl-N-methylmorpholinium bromide. To 16.68 g (9.33 mmol) of the obtained N-allyl-N-methylmorpholinium bromide, 75.70 g of methanol was added and stirred at room temperature. 11.35 g (5.25 mmol) of silver (I) oxide was added dropwise thereto over 1 hour and then stirred for 21 hours at room temperature. The resulting reaction solution was filtered and the residue was washed with 9.85 g of methanol to obtain methanol solution of N-allyl-N-methylmorpholinium hydroxide as a filtrate. 15.01 g (16.54 mmol) was drawn from the obtained methanol solution of N-allyl-N-methylmorpholinium hydroxide, and 1.53 g (16.98 mmol) of methoxyacetic acid was added thereto at room temperature followed by stirring for 12 hours at room temperature. The reaction solution was concentrated and dried to obtain 3.92 g of N-allyl-N-methylmorpholinium methoxyacetate (hereinbelow, abbreviated as [N$_{AMM}$] [MEAA]) (total yield: 100%).

$^1$H-NMR analysis data of the [N$_{AMM}$] [MEEPA] is given below.

$^1$H-NMR(DMSO-d$_6$) δ(ppm)=6.08(dt,1H), 5.19(dd,2H), 4.15(d,2H), 3.94(t,4H), 3.48(t,4H), 3.24(s,3H), 3.17(s,3H), 2.01(t,3H)

EXAMPLE 2-6

To a 5 L four neck flask, 632.52 g (3.49 mol) of N,N-diethyl-N-(2-methoxyethyl)-N-methylammonium chloride and 3168.18 g of methanol were added and stirred at room temperature. 445.02 g (1.92 mol) of silver (I) oxide was added thereto over 1 hour and stirred for 21 hours at room temperature. The reaction solution was filtered and the residue was washed with 173.55 g of methanol to obtain methanol solution of N,N-diethyl-N-(2-methoxyethyl)-N-methylammonium hydroxide as a filtrate. 20.02 g (19.60 mmol) was drawn from the obtained methanol solution of N,N-diethyl-N-(2-methoxyethyl)-N-methylammonium hydroxide, and 2.38 g (19.60 mmol) of 3-(methylthio) propanoic acid, which has been obtained from Preparation Example 3, was added thereto at room temperature followed by stirring for 12 hours at room temperature. The resulting reaction solution was concentrated and dried to obtain 5.50 g of N,N-diethyl-N-(2-methoxyethyl)-N-methylammonium 3-(methylthio)propanoate (hereinbelow, abbreviated as [N$_{221ME}$] [MSPA]) (total yield: 100%).

$^1$H-NMR analysis data of the obtained [N$_{221ME}$] [MSPA] is given below.

$^1$H-NMR(DMSO-d$_6$) δ(ppm)=3.68(t,2H), 3.58-3.45(m, 7H), 3.97(s,3H), 2.57-2.47(m,4H), 2.06-1.99(m,5H), 1.27(t, 6H)

EXAMPLE 2-7

The onium salt (1) was obtained in the same manner as Example 2-6 except that N,N-diethyl-N-(2-methoxyethyl)-N-methylammonium chloride of Example 2-6 was replaced with the halide salt (5) shown in Table 1.

$^1$H-NMR analysis data of the [N$_{211MEE}$] [MSPA] is given below.

$^1$H-NMR(DMSO-d$_6$) δ(ppm)=3.72(t,2H), 3.59-3.38(m, 8H), 3.27(s,3H), 2.93(s,3H), 2.54(br,4H), 2.03-2.00(m,6H), 1.23(t,3H)

EXAMPLE 2-8

To 20.07 g (23.88 mmol) of the methanol solution of N,N-diethyl-N-(2-methoxyethyl)-N-methylammonium hydroxide that was prepared in the same manner as Example 1-1, 4.28 g (22.27 mmol) of 3-[2-(2-methoxyethoxy)ethoxy]propanoic acid, which has been obtained in Preparation Example 1, was added at room temperature and stirred for 12 hours. The reaction solution was concentrated and dried to obtain 8.25 g of N,N-diethyl-N-(2-methoxyethyl)-N-methylammonium 3-[2-(2-methoxyethoxy)ethoxy]propanoate (hereinbelow, abbreviated as [N$_{221ME}$] [MEEEPA]) (total yield: 100%).

$^1$H-NMR analysis data of the [N$_{221ME}$] [MEEEPA] is given below.

$^1$H-NMR(CDCl$_3$) δ(ppm)=3.86-3.78(m,2H), 3.67-3.61 (m,6H), 3.61-3.49(m,4H), 3.38(s,6H), 3.21(s,3H), 2.51 (t,2H), 1.38(t,6H)

EXAMPLE 2-9

The onium salt (1) was obtained in the same manner as Example 2-8 except that 3-[2-(2-methoxyethoxy)ethoxy]propanoic acid of Example 2-8 was replaced with 4,7,10,13-tetraoxatetradecanoic acid.

$^1$H-NMR analysis data of the [N$_{221ME}$] [TOTA] is given below, $^1$H-NMR(CDCl$_3$) δ(ppm)=3.88(br,2H), 3.81-3.76(m,2H), 3.69-3.57(m,16H), 3.49(d,6H), 3.11(s,311), 2.54(t,2H), 0.98 (t,6H)

COMPARATIVE EXAMPLE 1-1

To a 100 mL four neck flask, 7.93 g (43.55 mmol) of N,N,N-trimethyl-N-propylammonium bromide and 40.44 g of methanol were added and stirred at room temperature. 5.56 g (24.00 mmol) of silver (I) oxide was added thereto over 15 minutes and then stirred for 5 hours at room temperature. The reaction solution was filtered and the residue was washed with 1.92 g of methanol to obtain methanol solution of N,N,N-trimethyl-N-propylammonium hydroxide as a filtrate. 30.01 g (23.36 mmol) was drawn from the resulting methanol solution of N,N,N-trimethyl-N-propylammonium hydroxide, and 1.41 g (23.48 mmol) of acetic acid was added thereto at room temperature followed by stirring for 12 hours at room temperature. The resulting reaction solution was concentrated and dried to obtain 3.97 g of N,N,N-trimethyl-N-propylammonium acetate (hereinbelow, abbreviated as [N$_{1113}$] [Ac]) (total yield: 100%).

$^1$H-NMR analysis data of the obtained [N$_{1113}$] [Ac] is given below.

$^1$H-NMR(CDCl$_3$) δ(ppm)=3.50-3.47(m,2H), 3.37(s,9H), 1.93(s,3H), 1.85-1.75(m,2H), 1.06(t,3H)

COMPARATIVE EXAMPLE 1-2

The onium salt shown in Table 1 was obtained in the same manner as Comparative Example 1-1 except that N,N,N-trimethyl-N-propylammonium bromide of Comparative Example 1-1 was replaced with the halide salt shown in Table 1.

$^1$H-NMR analysis data of the [N$_{221ME}$] [Ac] is given below, $^1$H-NMR(DMSO-d$_6$) δ(ppm)=3.73(br,2H), 3.49(t,2H), 3.37(q,4H), 3.31(s,3H), 2.98(s,3H), 1.57(s,3H), 1.22(t,6H)

COMPARATIVE EXAMPLE 2-1

The onium salt shown in Table 1 was obtained in the same manner as Example 1-4 except that 3-(2-methoxyethoxy) propanoic acid of Example 1-4 was replaced with acetic acid.

COMPARATIVE EXAMPLE 2-2

The onium salt shown in Table 1 was obtained in the same manner as Example 1-4 except that 1-ethyl-3-methylimidazolium chloride of Example 1-4 was replaced with the halide salt shown in Table 1 and 3-(2-methoxyethoxy)propanoic acid was replaced with acetic acid.

COMPARATIVE EXAMPLE 1-3

To a 1 L four neck flask, 90.02 g (496.88 mmol) of N,N-diethyl-N-(2-methoxyethyl)-N-methylammonium chloride and 367.43 g of methanol were added and stirred at room temperature. 57.59 g (248.52 mmol) of silver (I) oxide was added thereto over 15 minutes and then stirred for 21 hours at room temperature. The reaction solution was filtered and the residue was washed with 92.89 g of methanol to obtain methanol solution of N,N-diethyl-N-(2-methoxyethyl)-N-methylammonium hydroxide as a filtrate. To 7.32 g (6.10 mmol) of the resulting methanol solution of N,N-diethyl-N-(2-methoxyethyl)-N-methylammonium hydroxide, 0.99 g (6.10 mmol) of 2-aminopropanoic acid was added at room temperature followed by stirring for 12 hours at room temperature. The reaction solution was concentrated and dried to obtain 113.25 g of N,N-diethyl-N-(2-methoxyethyl)-N-methylammonium 2-aminopropanoate (hereinbelow, abbreviated as [N$_{221ME}$] [Ala]) (total yield: 98%).

$^1$H-NMR analysis data of the obtained [N$_{221ME}$] [Ala] is given below.

$^1$H-NMR(DMSO-d$_6$) δ(ppm)=3.72(br,2H), 3.52(t,2H), 3.39(q,4H), 3.28(s,3H), 2.99(s,3H), 2.79(m,1H), 1.19(t,6H), 0.98(d,3H)

TABLE 1

| Example | Halide salt (5) | Onium salt (1) | Obtained amount (g) |
|---|---|---|---|
| 1-1 | [N$_{221ME}$] [Cl] | [N$_{221ME}$] [MEEPA] | 1.69 |
| 1-2 | [N$_{1224}$] [Br] | [N$_{1224}$] [MEEPA] | 4.30 |
| 1-3 | [N$_{1113}$] [Br] | [N$_{1113}$] [MEEPA] | 3.59 |
| 2-1 | [N$_{211MEE}$] [Br] | [N$_{211MEE}$] [MEEPA] | 3.93 |
| 2-2 | [N$_{AMM}$] [Br] | [N$_{AMM}$] [MEEPA] | 4.80 |
| 1-4 | [C$_2$mim] [Cl] | [C$_2$mim] [MEEPA] | 2.38 |
| 1-5 | [C$_4$mim] [Cl] | [C$_4$mim] [MEEPA] | 9.38 |
| 1-6 | [N$_{221ME}$] [Cl] | [N$_{221ME}$] [EEEPA] | 1.99 |
| 1-7 | [N$_{1224}$] [Br] | [N$_{1224}$] [EEEPA] | 4.76 |

TABLE 1-continued

| | Halide salt | Onium salt | Obtained amount (g) |
|---|---|---|---|
| 1-8 | [C$_2$mim] [Cl] | [C$_2$mim] [EEEPA] | 2.38 |
| 2-3 | [N$_{221ME}$] [Cl] | [N$_{221ME}$] [MEAA] | 5.03 |
| 2-4 | [N$_{211MEE}$] [Br] | [N$_{211MEE}$] [MEAA] | 3.94 |
| 2-5 | [N$_{AMM}$] [Br] | [N$_{AMM}$] [MEAA] | 3.92 |
| 2-6 | [N$_{221ME}$] [Cl] | [N$_{221ME}$] [MSPA] | 5.50 |
| 2-7 | [N$_{211MEE}$] [Br] | [N$_{211MEE}$] [MSPA] | 4.36 |
| 2-8 | [N$_{221ME}$] [Cl] | [N$_{221ME}$] [MEEEPA] | 8.25 |
| 2-9 | [N$_{221ME}$] [Cl] | [N$_{221ME}$] [TOTA] | 9.63 |

| Comp. Example | Halide salt | Onium salt | Obtained amount (g) |
|---|---|---|---|
| 1-1 | [N$_{1113}$] [Br] | [N$_{1113}$] [Ac] | 3.97 |
| 1-2 | [N$_{221ME}$] [Cl] | [N$_{221ME}$] [Ac] | 7.33 |
| 2-1 | [C$_2$mim] [Cl] | [C$_2$mim] [Ac] | 1.02 |
| 2-2 | [C$_4$mim] [Cl] | [C$_4$mim] [Ac] | 2.14 |
| 1-3 | [N$_{221ME}$] [Cl] | [N$_{221ME}$] [Ala] | 113.25 |

EVALUATION EXAMPLE 1-1

In a sample tube, 1.00 g of N,N-diethyl-N-(2-methoxyethyl)-N-methylammonium 3-(2-methoxyethoxy)propanoate ([N$_{221ME}$] [MEEPA]) was placed and heated to 100° C. At 100° C., microcrystalline cellulose Avicel (registered trademark) was added in a portion of 0.01 g followed by stirring. When Avicel is found to be dissolved according to visual observation, 0.01 g of Avicel was additionally added and the same procedure was performed. Until no more cellulose is dissolved, the same procedure was repeated. As a result, it was confirmed that complete dissolution was obtained up to 0.24 g, but the cellulose did not fully dissolve at the time of adding 0.25 g. When 10 mL of methanol was added to the resulting solution at room temperature, the dissolved cellulose was precipitated. After adding methanol until no more cellulose is precipitated, the precipitated cellulose was filtered, washed with methanol, and dried under reduced pressure at room temperature to obtain cellulose. It was then confirmed that the mixture of N,N-diethyl-N-(2-methoxyethyl)-N-methylammonium 3-(2-methoxyethoxy)propanoate recovered as filtrate can be used as a recycled product after concentration under reduced pressure for removing methanol by distillation.

EVALUATION EXAMPLES 1-2 TO 1-8, 2-1 TO 2-9 AND COMPARATIVE EVALUATION EXAMPLES 1 TO 7

The experimental procedures were performed in the same manner as Evaluation Example 1-1 except that the onium salt shown in Table 2 was used instead of N,N-diethyl-N-(2-methoxyethyl)-N-methylammonium 3-(2-methoxyethoxy)propanoate of Evaluation Example 1-1. The results are shown in Table 2.

TABLE 2

| Evaluation Example | Onium salt (1) | Solubility |
|---|---|---|
| 1-1 | [N$_{221ME}$] [MEEPA] | 24 |
| 1-2 | [N$_{1224}$] [MEEPA] | 21 |
| 1-3 | [N$_{1113}$] [MEEPA] | 26 |
| 2-1 | [N$_{211MEE}$] [MEEPA] | 22 |
| 2-2 | [N$_{AMM}$] [MEEPA] | 17 |
| 1-4 | [C$_2$mim] [MEEPA] | 17 |
| 1-5 | [C$_4$mim] [MEEPA] | 17 |
| 1-6 | [N$_{211ME}$] [EEEPA] | 29 |
| 1-7 | [N$_{1224}$] [EEEPA] | 19 |
| 1-8 | [C$_2$mim] [EEEPA] | 17 |

TABLE 2-continued

| Evaluation Example | Onium salt (1) | Solubility |
|---|---|---|
| 2-3 | [N$_{221ME}$] [MEAA] | 25 |
| 2-4 | [N$_{211MEE}$] [MEAA] | 17 |
| 2-5 | [N$_{AMM}$] [MEAA] | 18 |
| 2-6 | [N$_{221ME}$] [MSPA] | 18 |
| 2-7 | [N$_{211ME}$] [MSPA] | 29 |
| 2-8 | [N$_{211ME}$] [MEEEPA] | 15 |
| 2-9 | [N$_{221ME}$] [TOTA] | 15 |

| Comparative Evaluation Example | Onium salt | Solubility |
|---|---|---|
| 1-1 | [C$_2$mim] [Cl] | 10 |
| 1-2 | [C$_2$mim] [Ac] | 8 |
| 1-3 | [C$_4$mim] [Cl] | 10 |
| 1-4 | [C$_4$mim] [Ac] | 12 |
| 1-5 | [N$_{1113}$] [Ac] | 0 |
| 1-6 | [N$_{221ME}$] [Ac] | 0 |
| 1-7 | [N$_{221ME}$] [Ala] | 13 |

EVALUATION EXAMPLE 2-10

In a sample tube, 030 g of N,N-diethyl-N-methyl-N-(2-methoxyethyl)ammonium methoxyacetate ([N$_{221ME}$] [MEEPA]) and 0.70 g of dimethyl sulfoxide were added and mixed. 1.00 g of the mixture solution was heated to 100° C. At 100° C., microcrystalline cellulose Avicel (registered trademark) was added in a portion of 0.01 g followed by stirring. When Avicel is found to be dissolved according to visual observation, 0.01 g of Avicel was additionally added and the same procedure was performed. Until no more cellulose is dissolved, the same procedure was repeated. As a result, it was confirmed that complete dissolution was obtained up to 0.13 g, but the cellulose did not fully dissolve when 0.14 g was added.

EVALUATION EXAMPLES 2-11 TO 2-15

The experimental procedures were performed in the same manner as Evaluation Example 2-10 except that dimethyl sulfoxide of Evaluation Example 2-10 was replaced with the organic solvent shown in Table 3 and use amount of N,N-diethyl-N-(2-methoxyethyl)-N-methylammonium methoxyacetate and organic solvent were adjusted to the amount shown in Table 3. The results are shown in Table 3.

COMPARATIVE EVALUATION EXAMPLE 2-1

In a sample tube, 1.00 g of dimethyl sulfoxide was placed followed by heating to 100° C. At 100° C., microcrystalline cellulose Avicel (registered trademark) was added in an amount of 0.01 g followed by stirring. However, Avicel did not fully dissolve.

COMPARATIVE EVALUATION EXAMPLES 2-2 AND 2-3

The experimental procedures were performed in the same manner as Comparative Evaluation Example 2-1 except that dimethyl sulfoxide of Comparative Evaluation Example 24 was replaced with the organic solvent shown in Table 3. The results are shown in Table 3. In Table 3, DMSO represents dimethyl sulfoxide, DMF represents N,N-dimethylformamide, and DMA represents N,N-dimethylacetamide.

TABLE 3

| | Use amount | Onium salt |

TABLE 3-continued

| Evaluation Example | Organic solvent | Use amount of organic solvent (g) | (1) Use amount (g) | Solubility |
|---|---|---|---|---|
| 2-10 | DMSO | 0.70 | 0.30 | 13 |
| 2-11 | DMSO | 0.50 | 0.50 | 15 |
| 2-12 | DMF | 0.70 | 0.30 | 9 |
| 2-13 | DMF | 0.50 | 0.50 | 6 |
| 2-14 | DMA | 0.70 | 0.30 | 12 |
| 2-15 | DMA | 0.50 | 0.50 | 18 |

| Comp. Evaluation Example | Organic solvent | Use amount of organic solvent (g) | Onium salt (1) Use amount (g) | Solubility |
|---|---|---|---|---|
| 2-1 | DMSO | 1.00 | 0 | Less than 1 |
| 2-2 | DMF | 1.00 | 0 | Less than 1 |
| 2-3 | DMA | 1.00 | 0 | Less than 1 |

INDUSTRIAL APPLICABILITY

According to the present invention, it is possible to provide an onium salt having an extremely high ability to dissolve cellulose at temperatures of 100° C. or lower. It also makes it possible to provide a liquid composition containing this onium salt and cellulose, as a composition suitable for the recovery of cellulose, and a method for recovering cellulose efficiently by using such a liquid composition containing the onium salt and cellulose.

The invention claimed is:

1. An onium salt consisting of Formula (1):

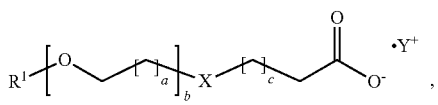

(1)

wherein a is an integer of 1 to 3, b is an integer of 0 to 6, c is an integer of 0 to 3, $R^1$ is a hydrocarbon group having 1 to 6 carbon atoms, X is an oxygen atom or a sulfur atom, and $Y^+$ is an onium cation having Formula (2), (3), or (4):

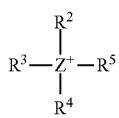

(2)

wherein $Z^+$ is a nitrogen ion or a phosphorus ion, and each of $R^2$, $R^3$, $R^4$, and $R^5$ is a hydrocarbon group having 1 to 20 carbon atoms optionally containing a heteroatom, provided that at least one of $R^2$, $R^3$, $R^4$, and $R^5$ is an alkoxyalkyl group, or alternatively each of $R^2$, $R^3$, $R^4$, and $R^5$ is independently selected from the group consisting of methyl, ethyl, propyl, and butyl;

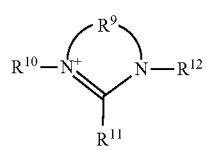

(3)

wherein $R^6$ is a hydrocarbon group having 4 to 20 carbon atoms optionally containing a heteroatom and each of le and $R^8$ is a hydrocarbon group having 1 to 20 carbon atoms optionally containing a heteroatom, provided that $R^8$ does not exist when the nitrogen ion has a double bond;

(4)

wherein $R^9$ is a hydrocarbon group having 2 to 20 carbon atoms optionally containing a heteroatom and each of $R^{10}$, $R^{11}$, and $R^{12}$ is a hydrogen atom or a hydrocarbon group having 1 to 20 carbon atoms optionally containing a heteroatom.

2. The onium salt according to claim 1, wherein b is 0 or 1.

3. The onium salt according to claim 1, wherein a is 1, b is 0 or 1, c is 0 or 1, and $R^1$ is a hydrocarbon group having 1 or 2 carbon atoms.

4. The onium salt according to claim 1, wherein at least one of $R^2$, $R^3$, $R^4$, and $R^5$ is an alkoxyalkyl group, at least one of $R^7$ and $R^8$ is an alkoxyalkyl group, and at least one of $R^{10}$, $R^{11}$, and $R^{12}$ is an alkoxyalkyl group.

5. The onium salt according to claim 1, wherein $Y^+$ is N,N-diethyl-N-methyl-N-(2-methoxyethyl)ammonium or N-ethyl-N-[2-(2-methoxyethoxy)ethyl]-N,N-dimethylammonium.

6. A mixed onium salt obtained by mixing two or more types of the onium salt according to claim 1.

7. A liquid composition comprising: cellulose; and the onium salt according to claim 1, the cellulose being dissolved in the onium salt.

8. A liquid composition comprising: cellulose; and a medium containing the onium salt according to claim 1 and an organic solvent, the cellulose being dissolved in the medium.

9. The liquid composition according to claim 8, wherein the organic solvent is selected from the group consisting of N,N-dimethylacetamide, dimethyl sulfoxide, N,N-dimethylformamide, and a mixture thereof.

10. A method for recovering cellulose comprising: dissolving cellulose in a medium containing the onium salt according to claim 1; and further mixing with a second solvent to precipitate the cellulose.

11. A method for recovering cellulose comprising: dissolving cellulose in a medium containing the onium salt according to claim 1 and an organic solvent; and further mixing with a second solvent to precipitate the cellulose.

12. The method for recovering cellulose according to claim 11, wherein the organic solvent is selected from the group consisting of N,N-dimethylacetamide, dimethyl sulfoxide, N,N-dimethylformamide, and a mixture thereof.

13. The onium salt according to claim 2, wherein $Y^+$ is an onium cation having Formula (2), (3), or (4):

Formula (2):

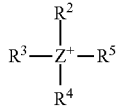

(2)

wherein $Z^+$ is a nitrogen ion or a phosphorus ion, and each of $R^2$, $R^3$, $R^4$, and $R^5$ is a hydrocarbon group having 1 to 20 carbon atoms optionally containing a heteroatom, Formula (3):

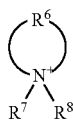

(3)

wherein $R^6$ is a hydrocarbon group having 4 to 20 carbon atoms optionally containing a heteroatom and each of $R^7$ and $R^8$ is a hydrocarbon group having 1 to 20 carbon atoms optionally containing a heteroatom, with the proviso that $R^8$ does not exist when the nitrogen ion has a double bond, Formula (4):

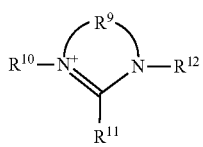

(4)

wherein $R^9$ is a hydrocarbon group having 2 to 20 carbon atoms optionally containing a heteroatom and each of $R^{10}$, $R^{11}$, and $R^{12}$ is a hydrogen atom or a hydrocarbon group having 1 to 20 carbon atoms optionally containing a heteroatom.

14. The onium salt according to claim 13, wherein at least one of $R^2$, $R^3$, $R^4$, and $R^5$ is an alkoxyalkyl group, at least one of $R^7$ and $R^8$ is an alkoxyalkyl group, and at least one of $R^{10}$, $R^{11}$, and $R^{12}$ is an alkoxyalkyl group.

15. The onium salt according to claim 3, wherein $Y^+$ is an onium cation having formula (2), (3), or (4):

Formula (2):

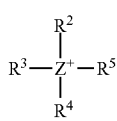

(2)

wherein $Z^+$ is a nitrogen ion or a phosphorus ion, and each of $R^2$, $R^3$, $R^4$, and $R^5$ is a hydrocarbon group having 1 to 20 carbon atoms optionally containing a heteroatom, Formula (3):

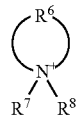

(3)

wherein $R^6$ is a hydrocarbon group having 4 to 20 carbon atoms optionally containing a heteroatom and each of $R^7$ and $R^8$ is a hydrocarbon group having 1 to 20 carbon atoms optionally containing a heteroatom, with the proviso that $R^8$ does not exist when the nitrogen ion has a double bond, Formula (4):

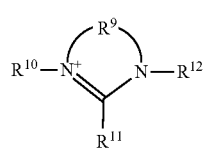

(4)

wherein $R^9$ is a hydrocarbon group having 2 to 20 carbon atoms optionally containing a hetero atom and each of $R^{10}$, $R^{11}$, and $R^{12}$ is a hydrogen atom or a hydrocarbon group having 1 to 20 carbon atoms optionally containing a heteroatom.

16. The onium salt according to claim 15, wherein at least one of $R^2$, $R^3$, $R^4$, and $R^5$ is an alkoxyalkyl group, at least one of $R^7$ and $R^8$ is an alkoxyalkyl group, and at least one of $R^{10}$, $R^{11}$, and $R^{12}$ is an alkoxyalkyl group.

17. A liquid composition comprising: cellulose; and the mixed onium salt according to claim 6, the cellulose being dissolved in the mixed onium salt.

18. A liquid composition comprising: cellulose; and a medium containing the mixed onium salt according to claim 6 and an organic solvent, the cellulose being dissolved in the medium.

19. A method for recovering cellulose comprising: dissolving cellulose in a medium containing the mixed onium salt according to claim 6; and further mixing with a second solvent to precipitate the cellulose.

20. A method for recovering cellulose comprising: dissolving cellulose in a medium containing the mixed onium salt according to claim 6 and an organic solvent; and further mixing it with a second solvent to precipitate the cellulose.

21. The onium salt according to claim 1, wherein $Y^+$ is an onium cation having Formula (2) or Formula (4).

* * * * *